(12) United States Patent
Yamauchi et al.

(10) Patent No.: US 11,633,715 B2
(45) Date of Patent: Apr. 25, 2023

(54) DNA COMPLEX, ADSORBENT, ADSORPTION COLUMN, PURIFICATION SYSTEM, LIQUID TREATMENT METHOD, AND METHOD FOR PRODUCING DNA COMPLEX

(71) Applicant: CANON KABUSHIKI KAISHA, Tokyo (JP)

(72) Inventors: Fumio Yamauchi, Yokohama (JP); Kengo Kanazaki, Yokohama (JP); Teigo Sakakibara, Tokyo (JP); Yoshinori Kotani, Yokohama (JP); Ryoko Ueyama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 311 days.

(21) Appl. No.: 16/830,084

(22) Filed: Mar. 25, 2020

(65) Prior Publication Data

US 2020/0222877 A1    Jul. 16, 2020

Related U.S. Application Data

(63) Continuation of application No. PCT/JP2018/034449, filed on Sep. 18, 2018.

(30) Foreign Application Priority Data

Sep. 29, 2017   (JP) .............................. JP2017-192060

(51) Int. Cl.
| | | |
|---|---|---|
| *B01J 20/24* | (2006.01) | |
| *B01J 20/10* | (2006.01) | |
| *B01J 20/28* | (2006.01) | |
| *C12N 15/11* | (2006.01) | |
| *C02F 1/28* | (2006.01) | |
| *B01D 15/10* | (2006.01) | |
| *B09B 3/00* | (2022.01) | |
| *C22B 3/20* | (2006.01) | |
| *B09B 3/10* | (2022.01) | |
| *C02F 101/20* | (2006.01) | |
| *C02F 103/08* | (2006.01) | |
| *B09B 101/30* | (2022.01) | |

(52) U.S. Cl.
CPC .............. *B01J 20/24* (2013.01); *B01D 15/10* (2013.01); *B01J 20/103* (2013.01); *B01J 20/2803* (2013.01); *B01J 20/28007* (2013.01); *B01J 20/28016* (2013.01); *B01J 20/28052* (2013.01); *B09B 3/10* (2022.01); *C02F 1/288* (2013.01); *C12N 15/11* (2013.01); *C22B 3/20* (2013.01); *B09B 2101/30* (2022.01); *C02F 1/281* (2013.01); *C02F 1/285* (2013.01); *C02F 2101/20* (2013.01); *C02F 2103/08* (2013.01)

(58) Field of Classification Search
CPC .... B01J 20/24; B01J 20/103; B01J 20/28007; B01J 20/2803; B01J 20/28016; B01J 20/28052; C02F 2101/20; C02F 1/288; C02F 1/285; C02F 1/281; B01D 15/10; B09B 3/0008; B09B 3/20; B09B 2220/06; C22B 3/20; C12N 15/11
See application file for complete search history.

(56) References Cited

U.S. PATENT DOCUMENTS

| | | | |
|---|---|---|---|
| 7,691,990 B2 * | 4/2010 | Zhang | ................ B01J 20/28033 530/358 |
| 2020/0230573 A1 * | 7/2020 | Kanazaki | ............... B01J 20/286 |

FOREIGN PATENT DOCUMENTS

| | | |
|---|---|---|
| JP | H10-175994 A | 6/1998 |
| JP | 2000-350597 A | 12/2000 |
| JP | 2006-700 A | 1/2006 |
| JP | 2008-200594 A | 9/2008 |
| JP | 2009-149505 A | 7/2009 |
| JP | 2013-517298 A | 5/2013 |
| JP | 2016-75655 A | 5/2016 |
| JP | 2016-133501 A | 7/2016 |

OTHER PUBLICATIONS

Ren et al., Analytical Chemistry, (2014), 86, 7494-7499.*
DNA3 sequence NEBioCalculator® of New England BioLabs Inc. (May 27, 2022).*
Insua et al., European Polymer Journal, (2016), v.81, p. 198-215.*
Taka-Aki Sasaki et al., "Ruthenium Removal from Water Using Nucleic-Acid Base-Immobilized Fibers", Bulletin of the Society of Sea Water Science, Japan, 69, 2015, pp. 98-104.

* cited by examiner

*Primary Examiner* — Yong L Chu
(74) *Attorney, Agent, or Firm* — Canon U.S.A., Inc., IP Division

(57) ABSTRACT

A DNA complex includes a carrier and DNA immobilized on the carrier. 80% or more by mass of the DNA is single-stranded DNA, the DNA has an average molecular weight of 500,000 or less, and the DNA content is more than 15% by mass and 50% or less by mass of the DNA complex. The carrier contains an inorganic material. The DNA complex has an average particle size of 10 μm or more.

17 Claims, 7 Drawing Sheets

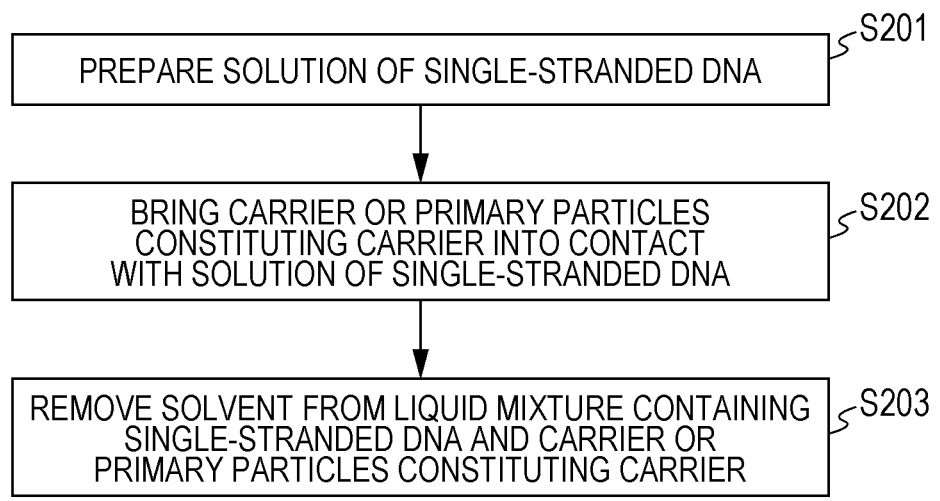

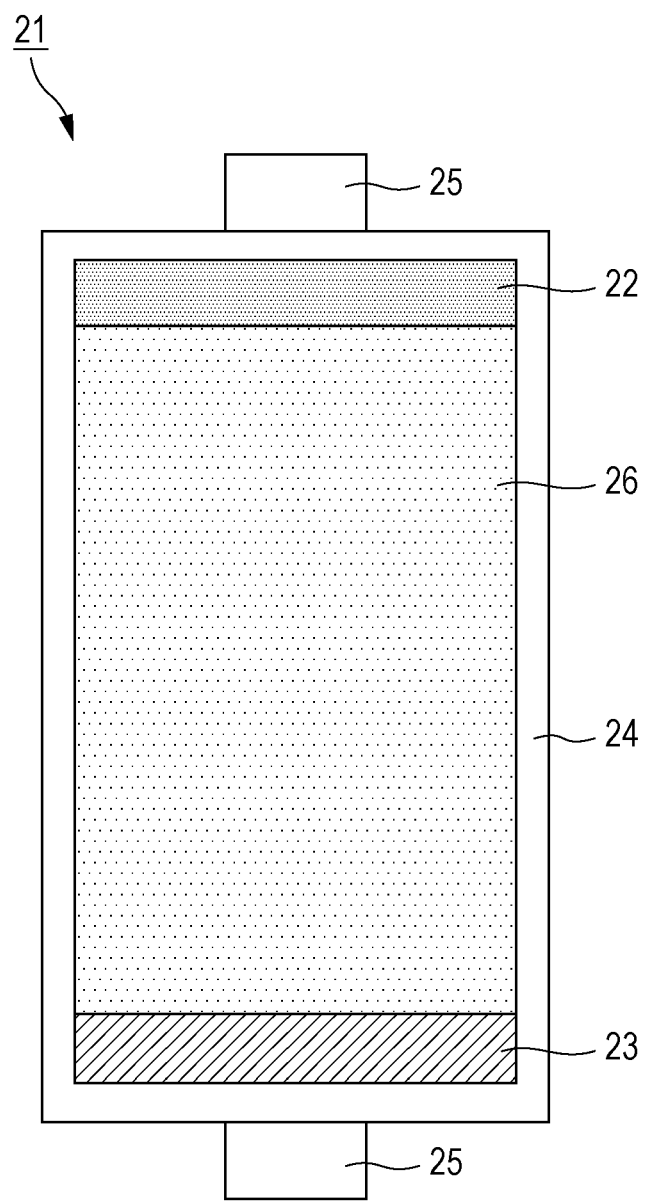

DNA COMPLEX, ADSORBENT, ADSORPTION COLUMN, PURIFICATION SYSTEM, LIQUID TREATMENT METHOD, AND METHOD FOR PRODUCING DNA COMPLEX

CROSS-REFERENCE TO RELATED APPLICATIONS

This application is a Continuation of International Patent Application No. PCT/JP2018/034449, filed Sep. 18, 2018, which claims the benefit of Japanese Patent Application No. 2017-192060, filed Sep. 29, 2017, both of which are hereby incorporated by reference herein in their entirety.

BACKGROUND OF THE INVENTION

Field of the Invention

The present disclosure relates to a DNA complex, an adsorbent, an adsorption column, a purification system, a liquid treatment method, and a method for producing a DNA complex.

Description of the Related Art

Solutions, such as waste fluids, from nuclear power plants, mechanical electronics industry, and chemical industry may contain heavy metals, noble metals, and ions thereof. It is desirable that these materials be removed from the solutions from the perspective of environmental conservation and reuse of the materials.

For example, melting or reusing a nuclear fuel in nuclear power plants produces a waste fluid containing radioactive or nonradioactive cesium (Cs), strontium (Sr), ruthenium (Ru), and iodine (I). Among these, Ru can have various valences due to coexisting ions in the aqueous solution and is therefore difficult to remove.

Ru may be removed from these waste fluids by a method of purifying a waste fluid through a column filled with an adsorbent. The adsorbent may be an ion-exchange resin or a polymer substrate having a low-molecular-weight polyamine compound, such as a nucleobase, as a side chain (Japanese Patent Application Laid-Open No. 2016-75655, Japanese Patent Application Laid-Open No. 2016-133501, and "Bulletin of the Society of Sea Water Science, Japan", 69, 2015, pp. 98-104).

SUMMARY OF THE INVENTION

It is known that ion-exchange resins used as adsorbents adsorb various types of metals and ions. Thus, for example, when a solution, like seawater, that contains large amounts of materials other than a target metal or ions, such as sodium ions or magnesium ions, is purified, large amounts of unintended materials are adsorbed, and the target material may not be sufficiently adsorbed.

Although radioactive Ru removers described in Japanese Patent Application Laid-Open No. 2016-75655, Japanese Patent Application Laid-Open No. 2016-133501, and "Bulletin of the Society of Sea Water Science, Japan", 69, 2015, pp. 98-104 can adsorb Ru even in aqueous solutions containing sodium chloride, the amount of adsorbed Ru is insufficient, and a further improvement in function is desired.

Thus, it has been difficult to efficiently adsorb and remove a target material from a liquid containing large amounts of impurities.

Accordingly, in view of such situations, the present disclosure aims to provide a DNA complex that can efficiently adsorb a target material from a liquid containing large amounts of impurities and provide an adsorption column, a purification system, and a liquid treatment method using the DNA complex.

A DNA complex according to one aspect of the present disclosure includes a carrier and DNA immobilized on the carrier, wherein 80% or more by mass of the DNA is single-stranded DNA, the DNA has an average molecular weight of 500,000 or less, the carrier contains an inorganic material, and the DNA complex has a number-average particle size of 10 µm or more.

A DNA complex according to another aspect of the present disclosure includes a carrier and DNA immobilized on the carrier, wherein 80% or more by mass of the DNA is single-stranded DNA, the DNA has an average molecular weight of 500,000 or less, and the carrier is a porous body.

A DNA complex according to another aspect of the present disclosure includes a carrier and DNA immobilized on the carrier, wherein 80% or more by mass of the DNA is single-stranded DNA, the carrier contains an inorganic material, and the DNA content is more than 15% by mass and 50% or less by mass of the DNA complex.

A DNA complex according to another aspect of the present disclosure includes a carrier and DNA immobilized on the carrier, wherein 80% or more by mass of the DNA is single-stranded DNA, and the carrier contains a layered metal hydroxide.

Further features of the present invention will become apparent from the following description of exemplary embodiments with reference to the attached drawings.

BRIEF DESCRIPTION OF THE DRAWINGS

FIG. 2 is a flow chart of an example of a method for producing a DNA complex.

FIG. 3 is a schematic view of an example of the structure of an adsorption column.

DESCRIPTION OF THE EMBODIMENTS

DNA complexes according to embodiments of the present disclosure are described below with reference to the accompanying drawings. The present disclosure is not limited to these embodiments. Various alterations and modifications can be made in these embodiments on the basis of the common knowledge of those skilled in the art without departing from the gist of the present disclosure. Such alterations and modifications also fall within the scope of the present disclosure.

[DNA Complex]

A DNA complex 1 according to an embodiment of the present disclosure is described below with reference to FIGS. 1A to 1C. The DNA complex 1 includes a carrier 11 and DNA 12 immobilized on the carrier 11. 80% or more by mass of the DNA 12 in the DNA complex 1 is single-stranded DNA. In the following description, the DNA 12 may also be referred to as single-stranded DNA 12.

Figure 1A:
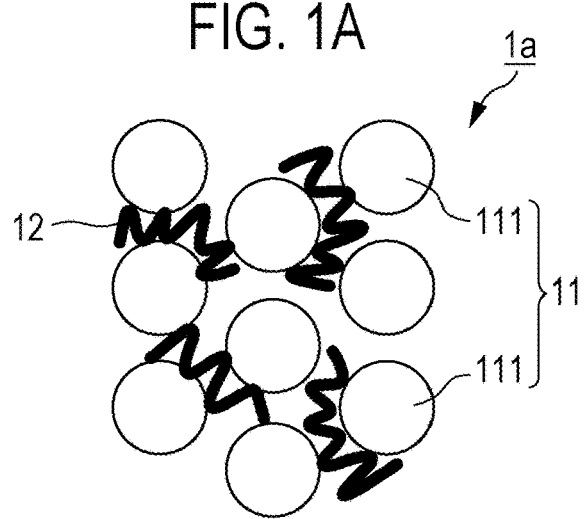
FIG. 1A is a schematic view of the structure of a DNA complex.
Figure 1B:
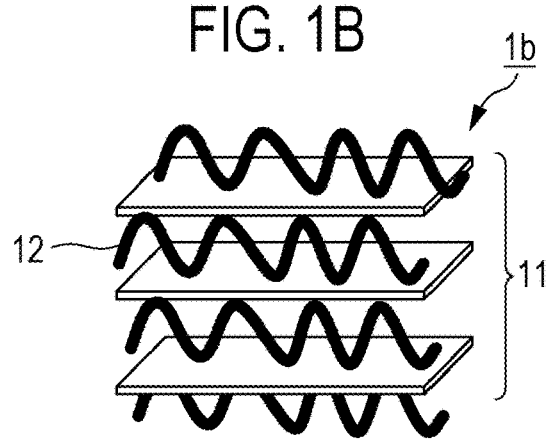
FIG. 1B is a schematic view of the structure of a DNA complex.
Figure 1C:
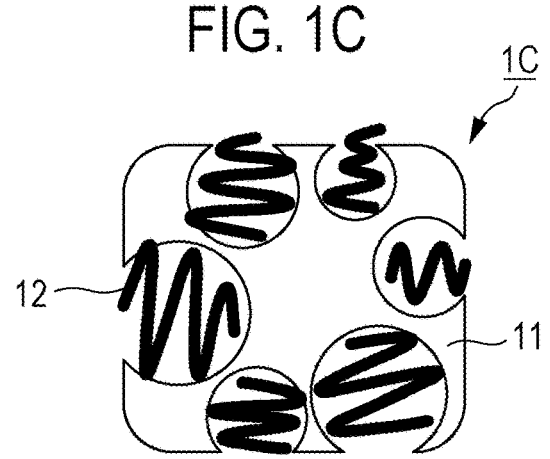
FIG. 1C is a schematic view of the structure of a DNA complex.

FIGS. 1A to 1C schematically illustrate the structures of DNA complexes 1 according to embodiments of the present disclosure (DNA complexes 1a to 1c). The DNA complex 1a in FIG. 1A includes the carrier 11 that is an aggregate of primary particles 111 and the DNA 12. The DNA complex 1b in FIG. 1B includes the carrier 11 that has a layered structure, such as a layered metal hydroxide, and the DNA 12. The DNA complex 1c in FIG. 1C includes the carrier 11 with many pores and the DNA 12.

In a first embodiment of the present disclosure, the carrier 11 contains an inorganic material. The DNA 12 has an average molecular weight of 500,000 or less. The DNA complex 1 has a number-average particle size of 10 μm or more.

In a second embodiment of the present disclosure, the carrier 11 is a porous body. The DNA 12 has an average molecular weight of 500,000 or less.

In a third embodiment of the present disclosure, the carrier 11 contains an inorganic material. The amount of the DNA 12 is more than 15% by mass and 50% or less by mass of the DNA complex 1.

In a fourth embodiment of the present disclosure, the carrier 11 contains a layered metal hydroxide.

The components of the DNA complex 1 are described below. In the following description, the DNA complex may be differently designated depending on the type of carrier. For example, the DNA complex is referred to as a DNA-immobilized silica for a silica carrier, a DNA-immobilized alumina for an alumina carrier, a DNA-immobilized hydrotalcite for a hydrotalcite carrier, or a DNA-immobilized activated carbon for an activated carbon carrier.

<Carrier 11>

The DNA complex 1 according to each embodiment of the present disclosure includes the carrier 11. The carrier 11 immobilizes and insolubilizes the DNA 12.

(Materials)

The carrier 11 preferably contains an inorganic material. The carrier 11 containing an inorganic material can have higher durability and heat resistance than the carrier 11 containing an organic resin or fiber or another organic material. Thermal degradation of the carrier 11 may cause the DNA 12 to be released. As described later, the DNA 12 has the function of adsorbing a material, such as metal ions. After the DNA 12 is released from the DNA complex 1, the DNA complex 1 used as an adsorbent has a significantly decreased adsorption capacity. The carrier 11 containing an inorganic material has improved durability and heat resistance and is less likely to release the DNA 12 even when exposed to a high-temperature environment. Thus, the DNA complex 1 can have a high adsorption capacity even in a high-temperature environment.

The carrier 11 preferably contains at least one inorganic material selected from the group consisting of metal oxides, layered metal hydroxides, activated carbon, and zeolite.

(Metal Oxides)

The metal oxides may be any oxides containing a metallic element and are preferably oxides containing at least one element selected from the group consisting of silicon (Si), aluminum (Al), titanium (Ti), and zirconium (Zr). The metal oxides are preferably at least one selected from the group consisting of silica, alumina, titania, and zirconia.

These metal oxides can be formed by hydrolysis and polycondensation of a metal alkoxide compound containing a metallic element.

For example, aluminum alkoxides, such as aluminum ethoxide, aluminum isopropoxide, aluminum n-butoxide, aluminum sec-butoxide, aluminum tert-butoxide, and aluminum acetylacetonate, may be used. Oligomers of these aluminum alkoxides may also be used. Silicon alkoxides, for example, $Si(OR)_4$ may be used. Rs may be different and independently denote a lower alkyl group, such as a methyl group, an ethyl group, a propyl group, an isopropyl group, a butyl group, or an isobutyl group. Titanium alkoxides, for example, tetramethoxytitanium, tetraethoxytitanium, tetra-n-propoxytitanium, tetraisopropoxytitanium, tetra-n-butoxytitanium, and tetraisobutoxytitanium may be used. Zirconium alkoxides, such as zirconium tetramethoxide, zirconium tetraethoxide, zirconium tetra-n-propoxide, zirconium tetraisopropoxide, zirconium tetra-n-butoxide, and zirconium tetra-tert-butoxide, may be used.

In the formation of a metal oxide by hydrolysis and polycondensation of a metal alkoxide compound, first, the metal alkoxide compound is dissolved in an organic solvent to prepare a solution. Examples of the organic solvent include alcohols, such as methanol, ethanol, butanol, ethylene glycol, and ethylene glycol mono-n-propyl ether; aliphatic and alicyclic hydrocarbons, such as n-hexane, n-octane, cyclohexane, cyclopentane, and cyclooctane; aromatic hydrocarbons, such as toluene, xylene, and ethylbenzene; esters, such as ethyl formate, ethyl acetate, n-butyl acetate, ethylene glycol monomethyl ether acetate, ethylene glycol monoethyl ether acetate, and ethylene glycol monobutyl ether acetate; ketones, such as acetone, methyl ethyl ketone, methyl isobutyl ketone, and cyclohexanone; and ethers, such as dimethoxyethane, tetrahydrofuran, dioxane, and diisopropyl ether. Among these, alcohols are preferably used in terms of the stability of a solution prepared.

In the preparation of a solution by dissolving an alkoxide compound in an organic solvent, if necessary, a catalyst and water may be added to promote the hydrolysis and polycondensation of the alkoxy group. Examples of the catalyst include, but are not limited to, nitric acid, hydrochloric acid, sulfuric acid, phosphoric acid, acetic acid, and ammonia.

Due to their high reactivity with water, aluminum alkoxides, titanium alkoxides, and zirconium alkoxides are rapidly hydrolyzed by contact with water contained in the air or by the addition of water and cause cloudiness or precipitation in the solution. To reduce cloudiness and precipitation, a stabilizer may be added in the preparation of the solution, as required. Examples of the stabilizer include β-diketone compounds, such as acetylacetone, dipivaloylmethane, trifluoroacetylacetone, hexafluoroacetylacetone, benzoylacetone, and dibenzoylmethane; β-keto ester compounds, such as methyl acetoacetate, ethyl acetoacetate, allyl acetoacetate, benzyl acetoacetate, iso-propyl acetoacetate, tert-butyl acetoacetate, iso-butyl acetoacetate, 2-methoxyethyl acetoacetate, and 3-keto-n-valeric acid methyl; and alkanolamines, such as monoethanolamine, diethanolamine, and triethanolamine. The mole ratio of the stabilizer to the metal alkoxide compound preferably ranges from 0.5 to 1.5, more preferably approximately 1.

A metal oxide containing two or more metallic elements may be formed by preparing and mixing a plurality of metal alkoxide compound solutions before hydrolysis and polycondensation.

(Layered Metal Hydroxides)

The layered metal hydroxides may be hydrotalcite, hydrocalumite, and pyroaurite, particularly preferably hydrotalcite. The layered metal hydroxides are also referred to as layered composite hydroxides. The hydrotalcite may be represented by the following general formula (1).

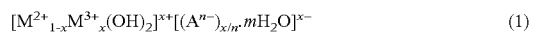

$$[M^{2+}_{1-x}M^{3+}_{x}(OH)_2]^{x+}[(A^{n-})_{x/n} \cdot mH_2O]^{x-} \quad (1)$$

$M^{2+}$ denotes at least one divalent metal ion selected from $Mg^{2+}$, $Zn^{2+}$, $Ca^{2+}$, $Fe^{2+}$, $Mn^{2+}$, $Co^{2+}$, $Ni^{2+}$, and $Cu^{2+}$, and $M^{3+}$ denotes at least one trivalent metal ion selected from $Al^{3+}$, $Fe^{3+}$, $Cr^{3+}$, $Ga^{3+}$, $La^{3+}$, and $Co^{3+}$. $A^{n-}$ denotes at least one n-valent anion selected from $SO_4^{2-}$, $Cl^-$, $CO_3^{2-}$, $OH^-$, and silicon oxyacid ions, x is in the range of $0.20 \leq x \leq 0.33$, and m denotes an integer. The hydrotalcite may be a purified natural product or a synthetic product.

(Activated Carbon, Zeolite)

The carrier 11 may contain activated carbon or zeolite. Activated carbon and zeolite are porous materials with a high specific surface area and are suitable for the carrier 11. Activated carbon and zeolite are preferred due to their high thermal stability and resistance to chemicals, such as acids and alkalis.

(Shape)

The carrier 11 is preferably a porous body. As described later, the DNA 12 is immobilized on the surface (the outer surface and the inner surface) of the carrier 11. The carrier 11 made of a porous body has a large specific surface area and a large region on which the DNA 12 can be immobilized, thus enabling a larger amount of the DNA 12 to be immobilized thereon. This can increase the amount of the DNA 12 in the DNA complex 1. As described later, the DNA 12 has the function of adsorbing a material, such as metal ions, and the amount of the material adsorbed increases with the amount of the DNA 12 in the DNA complex 1.

Furthermore, the carrier 11 itself can adsorb ions containing a metallic element, such as cesium, strontium, or ruthenium, or iodine. Thus, an increased specific surface area of the carrier 11 can result not only in an increased amount of the DNA 12 but also in an increased amount of adsorption on the carrier 11 itself. In the carrier 11 made of a porous body, the adsorption selectivity of a material, such as metal ions, varies with the pore size of the carrier 11 (for example, due to the molecular sieve effects). Thus, the carrier 11 is preferably a porous body. The carrier 11 made of a porous body can immobilize the DNA 12 inside of the carrier 11 such as inside of the pores or between layers of the carrier 11. The DNA 12 immobilized inside of the carrier 11 is less likely to come into contact with relatively coarse external materials, such as bacteria or DNA inactivating molecules (for example, deoxyribonuclease), than the DNA 12 immobilized on the outer surface of the carrier 11. Thus, the DNA 12 immobilized inside of the carrier 11 is protected from the attacks of bacteria or DNA inactivating molecules and is stable for extended periods. Thus, the carrier 11 is preferably a porous body.

The carrier 11 is preferably an aggregate of the primary particles 111. In this case, the primary particles 111 in the aggregate are preferably bonded together through a three-dimensional network. Such an aggregate can be considered to be a porous body with pores formed by the spaces between the primary particles. For the above reason, this can increase the amount of material, such as metal ions, adsorbed. Although described in detail later, the amount of the DNA 12 inside of the pores can be increased by mixing a colloidal solution of the primary particles 111 and a DNA solution to form an aggregate. Thus, the carrier 11 is preferably an aggregate of the primary particles 111. The aggregate is also referred to as an agglomerate.

The primary particles 111 in the aggregate preferably have an average particle size (diameter) in the range of 1 to 100 nm, more preferably 1 to 25 nm. The average particle size of the primary particles 111 in the aggregate can be measured by a method including the measurement of the specific surface area of the aggregate. More specifically, the specific surface area and density of the aggregate are measured and, on the assumption that the primary particles 111 in the aggregate are spheres with a uniform particle size, the average particle size can be calculated from the specific surface area and density. The specific surface area of the aggregate can be measured by any method. For example, the BET specific surface area measured by a gas adsorption method can be considered to be the specific surface area of the aggregate. The specific surface area measured by the Sears' method may also be considered to be the specific surface area of the aggregate.

The aggregate can be formed by aggregating or agglomerating fine particles that become the primary particles 111. The aggregate may be formed by any method, for example, by removing a dispersion medium or solvent from a dispersion or solution of fine particles, such as a colloidal solution. Preferably, the formation of the aggregate and the immobilization of the DNA 12 on the aggregate are simultaneously performed by mixing a dispersion or solution of the primary particles 111 with a solution of the DNA 12 and removing the dispersion medium and/or solvent. This enables the DNA 12 to be inserted into the spaces between the primary particles 111 in the aggregate and can increase the amount of the DNA 12. The aggregate may be formed by vacuum drying or spray drying.

In the aggregate, the primary particles 111 may be bonded together via a noncovalent bond and/or a covalent bond. Alternatively, as described later, the primary particles 111 may be bonded together through a cross-linking component via a covalent bond and/or a noncovalent bond. The covalent bond may be a siloxane bond, which is suitable for the primary particles 111 containing silica. The primary particles 111 can be bonded by a method (hereinafter also referred to as a cross-linking method) appropriately selected according to the type of the primary particles 111, for example, by volatilizing the dispersion medium or solvent or by drying. These treatments may be performed under heat conditions, if necessary. The cross-linking method may also utilize another stimulus, such as light.

The fine particles to form the aggregate (the primary particles 111) may be a colloidal metal oxide, such as colloidal silica, colloidal aluminum oxide, colloidal iron oxide, colloidal gallium oxide, colloidal lanthanum oxide, colloidal titanium oxide, colloidal cerium oxide, colloidal zirconium oxide, colloidal tin oxide, or colloidal hafnium oxide. These may be used alone or in combination. Among these, colloidal silica is preferably used as a main component of the primary particles 111 from the economic point of view.

Examples of commercial colloidal solutions containing dispersed colloidal silica include Snowtex 30, Snowtex N, Snowtex O, Snowtex C, Snowtex CM, Snowtex CXS, Organosilicasol IPA-ST, and Organosilicasol EG-ST (manufactured by Nissan Chemical Industries, Ltd., "Snowtex" is a trademark of Nissan Chemical Industries, Ltd.). Examples of commercial colloidal aluminum oxides include Aluminasol AS-200 (manufactured by Nissan Chemical Industries, Ltd.).

The carrier 11 may be secondary particles formed by binding primary particles together in advance or an aggregate (tertiary particles) of secondary particles. Examples of the secondary particles include chain-like silica, pearl-necklace-like silica, and fumed silica.

(Cross-Linking Component)

The cross-linking component for binding primary particles together may be any cross-linking component that is dispersed or dissolved in a dispersion medium of a primary particle dispersion liquid and that can cross-link and insolubilize the primary particles by drying. The cross-linking component may be an organic component or an inorganic component. For example, the organic component may be a radical polymerizable organic compound, an ionic organic compound, or an organic polymer. The radical polymerizable organic compound, such as a radical polymerizable monomer, a radical polymerizable oligomer, or a radical polymerizable polymer, can undergo radical polymerization by light or heat and cross-link primary particles. Upon a change in the concentration of salt in a solution or volatilization of a component, an ionic polymer, such as an anionic organic polymer or a cationic organic polymer, can aggregate and cross-link primary particles. An anionic polymer can aggregate by a reaction with a metal ion and cross-link primary particles. The inorganic component is preferably a metal salt compound, a metal alkoxide, a metal complex, an organosilane, or a hydrolysate thereof.

The metal salt compound may be a compound that is soluble in water and that finally becomes aluminum oxide, for example, $AlCl_3$, $Al(NO_3)_3$, or $NaAlO_2$. Another similar solidified oxide may be $TiOCl_2$ or $ZrOCl_2$. A partially cross-linked substance, for example, a dispersion liquid of a partially cross-linked substance of $AlCl_3$, such as $Al_4(OH)_9Cl_3$ or $Al_2(OH)_5Cl$ (highly basic aluminum chloride), may also be conveniently used.

Examples of the metal alkoxide include alkoxysilanes, such as tetramethoxysilane, tetraethoxysilane, and tetrapropoxysilane, aluminum alkoxides, such as aluminum ethoxide, aluminum isopropoxide, aluminum n-butoxide, aluminum sec-butoxide, and aluminum tert-butoxide, titanium alkoxides, such as tetramethoxytitanium, tetraethoxytitanium, tetra-n-propoxytitanium, tetraisopropoxytitanium, tetra-n-butoxytitanium, and tetraisobutoxytitanium, and zirconium alkoxides, such as zirconium tetramethoxide, zirconium tetraethoxide, zirconium tetra-n-propoxide, zirconium tetraisopropoxide, zirconium tetra-n-butoxide, and zirconium tetra-t-butoxide. Examples of the metal complex include chelate compounds, such as aluminum acetate, titanium acetate, tris(acetylacetonato) aluminum (III), bis(acetylacetonato) mono(propoxy) aluminum (III), mono(acetylacetonato) bis(propoxy) aluminum (III), tris(ethylacetoacetate) aluminum (III), tris(diethylmalonate) aluminum (III), bis(acetylacetonato) copper (II), tetrakis(acetylacetonato) zirconium (IV), tris(acetylacetonato) chromium (III), tris(acetylacetonato) cobalt (III), and titanium oxide (II) acetylacetonate $[(CH_3COCHCOCH_3)_2TiO]$. Examples of the organosilane include methyltrimethoxysilane, methyltriethoxysilane, phenyltrimethoxysilane, phenyltriethoxysilane, and dimethyldimethoxysilane. Oligomers produced by cross-linking these metal alkoxides, metal complexes, and organosilanes in advance may also be used.

If necessary, two or more different cross-linking components may be used in combination.

A cross-linking component that can gel due to a change in pH may also be used. Gelation refers to the promotion of cross-linking of primary particles by the addition of an acid, alkali, salt, or another component that has a pH shift effect. The cross-linking component that can gel particularly preferably contains an acidic component. The acidic component refers to a component that can react with an alkali ion, an alkaline-earth ion, or an ammonium ion and form a salt. More specifically, the acidic component may be a $Cl^-$, $NO_3^-$, $HSO_4^-$, or $SO_4^{2-}$ ion, or free hydrochloric acid, free nitric acid, free sulfuric acid, or free acetic acid, or β-diketone. These acidic components may also be used in combination, as required. The pH range of a reaction system for the gelation of the cross-linking component ranges preferably from 0 to 7, more preferably 1 to 6.

The cross-linking component may also be an alkoxysilane or a silane coupling agent.

In the present specification, cross-linking of primary particles may also be referred to as reinforcement of primary particles. The treatment or process of cross-linking primary particles may also be referred to as a reinforcement treatment or process. A compound that can cross-link primary particles is referred to as a cross-linking component or a reinforcement component. A solution containing the cross-linking component may also be referred to as a cross-linking liquid, a reinforcement liquid, or a reinforcement treatment liquid. Thus, cross-linking and reinforcement have the same meaning in the present specification.

(Surface Modification)

The carrier 11 may have an organosiloxane with a basic functional group or an epoxy group on its surface. The basic functional group is a functional group containing nitrogen, typically an amino group, that can form an acid-base structure with an acidic functional group, a phosphate group, of the DNA 12. The basic functional group, if present, in the carrier 11 can have an ionic interaction with the phosphate group of the DNA 12 and form a covalent bond or a noncovalent bond, thereby immobilizing the DNA 12. The basic functional group in the carrier 11 is preferably a secondary, tertiary, or quaternary amino group. The epoxy group, if present, in the carrier 11 can form a covalent bond with a basic group or a hydroxy group of the DNA 12 and thereby immobilize the DNA 12.

A basic functional group or an epoxy group may be introduced onto the surface of the carrier 11 by hydrolyzing a silane compound having this functional group (hereinafter also referred to as a coupling agent) on the surface of the carrier 11. The hydrolyzed silane compound can form a siloxane bond with a hydroxy group on the surface of the carrier 11 and thereby introduce the functional group onto the surface of the carrier 11.

Examples of the silane compound with a basic functional group include compounds represented by the following formulae (2) to (6).

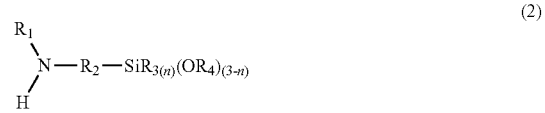

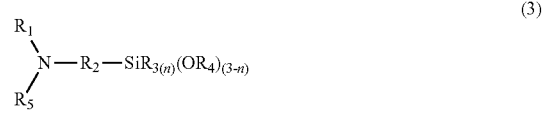

-continued

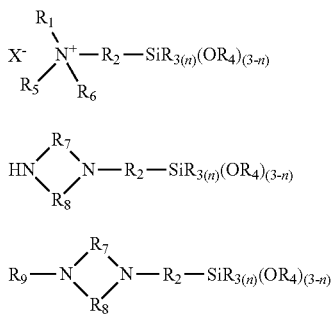

In the formulae, $R_1$ denotes hydrogen atm or a monovalent hydrocarbon group having 1 to 8 carbon atoms, and $R_3$, $R_4$, $R_5$, $R_6$, and $R_9$ independently denote a monovalent hydrocarbon group having 1 to 8 carbon atoms. $R_7$ and $R_8$ independently denote a divalent hydrocarbon group, and $R_2$ denotes a divalent hydrocarbon group having 1 to 8 carbon atoms or a divalent group having —NH—.

In these formulae (2) to (6), the monovalent hydrocarbon group having 1 to 8 carbon atoms denoted by $R_1$, $R_3$, $R_4$, $R_5$, $R_6$, or $R_9$ may be a linear, branched, or cyclic alkyl group having 1 to 8 carbon atoms, such as a methyl group, an ethyl group, a n-propyl group, an iso-propyl group, a n-butyl group, an iso-butyl group, a tert-butyl group, a n-pentyl group, a n-hexyl group, a n-heptyl group, or a n-octyl group, or an aromatic hydrocarbon group, such as a phenyl group. In the formulae (2) to (6), the divalent hydrocarbon group having 1 to 8 carbon atoms denoted by $R_2$ may be a linear, branched, or cyclic divalent alkylene group having 1 to 8 carbon atoms, such as a methylene group, an ethylene group, a trimethylene group, or a tetramethylene group, or a divalent aromatic hydrocarbon group having 1 to 8 carbon atoms, such as an o-phenylene group, a m-phenylene group, or a p-phenylene group, and the divalent group having —NH— may specifically be —NH— or a group formed by bonding a nitrogen atom to one or two divalent hydrocarbon groups, such as a methylene group, an ethylene group, a trimethylene group, and/or a tetramethylene group, more specifically, —$C_2H_4NHC_3H_6$—, —$C_3H_6NHC_2H_4$—, —$CH_2NHC_3H_6$—, —$C_2H_4NHCH_2$—, —$C_2H_4NHC_2H_4$—, or —$C_3H_6NHC_3H_6$— (the alkylene groups in these groups may be linear or branched). In the formulae (5) and (6), the divalent hydrocarbon group denoted by $R_7$ or $R_8$ may have any number of carbon atoms and may be a linear, branched, or cyclic divalent alkylene group, such as a methylene group, an ethylene group, a trimethylene group, or a tetramethylene group, or a divalent aromatic hydrocarbon group, such as an o-phenylene group, a m-phenylene group, or a p-phenylene group, more specifically, a methylene group or an ethylene group. In the formula (4), the anion denoted by $X^-$ may be any anion that can form a counter ion of a siloxane cation having a quaternary amino group, for example, a halide ion.

Specific examples of these silane compounds include $H_2NC_3H_6Si(OCH_3)_3$, $H_2NC_3H_6SiCH_3(OCH_3)_2$, $H_2NC_3H_6Si(OC_2H_5)_3$, $H_2NC_3H_6SiCH_3(OC_2H_5)_2$, $(CH_3)HNC_3H_6Si(OCH_3)_3$, $(CH_3)HNC_3H_6SiCH_3(OCH_3)_2$, $(CH_3)HNC_3H_6Si(OC_2H_5)_3$, $(CH_3)HNC_3H_6SiCH_3(OC_2H_5)_2$, $(CH_3)_2NC_3H_6Si(OCH_3)_3$, $(CH_3)_2NC_3H_6SiCH_3(OCH_3)_2$, $(CH_3)_2NC_3H_6Si(OC_2H_5)_3$, $(CH_3)_2NC_3H_6SiCH_3(OC_2H_5)_2$, $(C_2H_5)_2NC_3H_6Si(OCH_3)_3$, $(C_2H_5)_2NC_3H_6Si(OC_2H_5)_3$, $H_2NC_2H_4NHC_3H_6Si(OCH_3)_3$, $H_2NC_2H_4NHC_3H_6SiCH_3(OCH_3)_2$, $H_2NC_2H_4NHC_3H_6Si(OC_2H_5)_3$, $H_2NC_2H_4NHC_3H_6SiCH_3(OC_2H_5)_2$, $(CH_3)HNC_2H_4NHC_3H_6Si(OCH_3)_3$, $(CH_3)HNC_2H_4NHC_3H_6SiCH_3(OCH_3)_2$, $(CH_3)HNC_2H_4NHC_3H_6Si(OC_2H_5)_3$, $CH_3HNC_2H_4NHC_3H_6SiCH_3(OC_2H_5)_2$, $(CH_3)_2NC_2H_4NHC_3H_6Si(OCH_3)_3$, $(CH_3)_2NC_2H_4NHC_3H_6SiCH_3(OCH_3)_2$, $(CH_3)_2NC_2H_4NHC_3H_6Si(OC_2H_5)_3$, $(CH_3)_2NC_2H_4NHC_3H_6SiCH_3(OC_2H_5)_2$, and $Cl^-(CH_3)_3N^+C_3H_6Si(OCH_3)_3$, $Cl^-(C4H9)_3N^+C_3H_6Si(OCH_3)_3$. At least one of these may be used.

Specific examples of a coupling agent with a cyclic basic functional group include silane compounds represented by the following formulae (7) to (13).

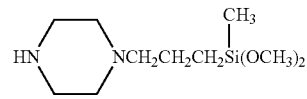

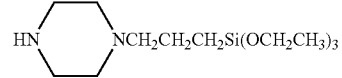

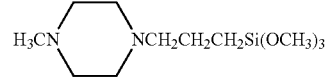

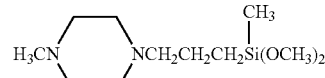

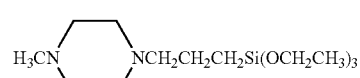

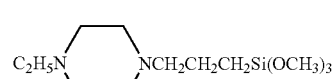

A specific example of a silane compound with an epoxy group is 3-glycidoxypropyltrimethoxysilane.

The silane compounds represented by the formulae (7) to (13) may be alkoxy oligomers that are partial hydrolytic condensates of the silane compounds. An increased number of reaction sites with the surface of the carrier 11 can stabilize the bonding between a silane compound and the surface of the carrier 11 and securely immobilize DNA. An alkoxy oligomer of the silane compound represented by the formula (10) does not destabilize a colloidal silica solution containing DNA (does not cause gelation) when added to the solution and is therefore a preferred silane compound with a basic functional group.

<DNA 12>

The DNA complex 1 according to each embodiment of the present disclosure includes the DNA 12 immobilized on the carrier 11. The DNA 12 may be replaced with RNA. Thus, a nucleic acid complex that includes the carrier 11 and a nucleic acid immobilized on the carrier 11 may also be used.

(Single-Stranded DNA)

80% or more by mass of the DNA 12 in the DNA complex 1 is single-stranded DNA. The single-stranded DNA constituting 80% or more by mass of the DNA 12 can result in an increased amount of the DNA 12 immobilized on the carrier 11. Although bases in double-stranded DNA form a hydrogen bond with their complementary bases with which base pairs can be formed, single-stranded DNA has no hydrogen bond. Thus, an amino group and other groups of bases in DNA are exposed, and this promotes the interaction between the bases and a material such as ions containing a metallic element or iodine. This results in the formation of a complex of a material, such as metal ions, and a higher adsorption capacity than double-stranded DNA.

A material, such as ions containing at least one element selected from the group consisting of metallic elements and iodine, to be adsorbed by the DNA 12 or the DNA complex 1 is hereinafter referred to as a target material to be removed. The target material to be removed is preferably an ion containing at least one element selected from the group consisting of cesium (Ce), strontium (Sr), ruthenium (Ru), lead (Pb), cadmium (Cd), zinc (Zn), copper (Cu), iron (Fe), nickel (Ni), silver (Ag), rhodium (Rh), palladium (Pd), iridium (Ir), iodate (IO), and iodine (I). The target material to be removed may contain a radioactive element. The DNA complex 1 according to each embodiment of the present disclosure is used to particularly preferably adsorb ions containing ruthenium (Ru), more preferably ions containing radioactive ruthenium.

DNA has four bases of adenine (A), thymine (T), guanine (G), and cytosine (C) at high densities in its molecular chain. Thus, DNA has a large number of sites on which the target material to be removed is adsorbed and can adsorb a large amount of the target material to be removed. Probably DNA can utilize a three-dimensional space formed by a polymer chain and can selectively adsorb metallic elements and iodine. More specifically, the contiguous base sequence and three-dimensional space of DNA easily produce a chelate effect. The chelate effect means that an increased number of ligands improve the complex stability between the ligands and a metallic element. For example, nitrogen atoms and oxygen atoms of bases in DNA can serve as ligands and form a stable complex with a metallic element, such as ruthenium. Thus, the DNA complex 1 can be used to reliably adsorb metallic elements.

The ratios of single-stranded DNA and double-stranded DNA to the whole DNA contained in the DNA complex 1 can be calculated by measuring absorbance. Alternatively, a commercial assay kit, for example, a PicoGreen dsDNA assay kit or an OliGreen ssDNA assay kit (manufactured by Thermo Fisher Scientific, "PicoGreen" and "OliGreen" are trademarks of Thermo Fisher Scientific) can be used in measurement according to their protocols.

(Average Molecular Weight)

The DNA 12 preferably has an average molecular weight of 500,000 or less. The DNA 12 more preferably has an average molecular weight of 200,000 or less, still more preferably less than 100,000, still more preferably 80,000 or less, particularly preferably 50,000 or less. For the DNA 12 with an average molecular weight of 500,000 or less, an increased amount of the DNA 12 immobilized on the carrier 11 can adsorb an increased amount of the target material to be removed.

The average molecular weight of the DNA 12 is an important factor in consideration of immobilization of the DNA 12 in a nanoscale space. For example, if the DNA 12 has a molecular weight of 500,000, is single-stranded DNA, and is adsorbed on the carrier surface, then the DNA 12 has an estimated size (radius of gyration) of approximately 15 nm. DNA of approximately this size or smaller can be efficiently immobilized on the carrier 11. Thus, the DNA 12 preferably has an average molecular weight of 500,000 or less.

The DNA 12 with an average molecular weight of 500,000 or less can have improved solubility in water, and an aqueous solution of the DNA 12 dissolved in water can have a decreased viscosity. In the production of the DNA complex 1 by a method including bringing an aqueous solution of the DNA 12 into contact with the carrier 11 or the primary particles constituting the carrier 11, the aqueous solution of the DNA 12 and the carrier 11 or the primary particles constituting the carrier 11 are preferably mixed as homogeneously as possible. An excessively high viscosity of the aqueous solution of the DNA 12 may make homogeneous mixing difficult, result in an insufficient amount of the DNA 12 in the DNA complex 1, and even make it difficult to produce the DNA complex 1. Thus, the DNA 12 preferably has an average molecular weight of 500,000 or less.

(DNA Content of DNA Complex)

The amount of the DNA 12 in the DNA complex 1 ranges preferably from 3% to 50% by mass, more preferably 5% to 50% by mass, of the DNA complex 1. The amount of the DNA 12 is still more preferably more than 15% by mass and 50% or less by mass. When the amount of the DNA 12 is 3% or more by mass, a larger amount of the target material to be removed can be adsorbed. In the DNA complex 1, the adsorption amount of the target material to be removed increases with the amount of the DNA 12, and therefore the amount of the DNA 12 is preferably increased. When the amount of the DNA 12 is more than 15% by mass, the adsorption amount of the target material to be removed can be significantly increased. When the amount of the DNA 12 is much more than 50% by mass, however, it may be difficult to stably immobilize the DNA 12 on the carrier 11. Thus, the amount of the DNA 12 is preferably 50% or less by mass.

The amount of the DNA 12 in the DNA complex 1 can be determined by an absorbance measurement method. More specifically, in the production of the DNA complex 1, the amount of DNA not immobilized on the carrier 11 and remaining in the solution may be determined by the absorbance measurement method. Alternatively, the amount of the DNA 12 can be determined by X-ray photoelectron spectroscopy (XPS) in surface analysis. In the measurement of the amount of the DNA 12 by XPS, a known amount of DNA is immobilized on the carrier surface to prepare a standard sample, and the amount of phosphorus measured by XPS is compared with that of the standard sample.

(Type of DNA)

The DNA 12 may be DNA obtained from testes and thymi of animals, such as mammals, birds, fish, and molluscs. In particular, DNA obtained from milt (testes) of salmon, herring, or cod or gonads of scallops is preferred. DNA obtained from thymi of mammals or birds, such as cattle, pigs, or chickens, is preferred. The DNA 12 may be synthesis DNA, may have any base sequence, and may be synthesis DNA with poly(dA), poly(dT), or another sequence. Alkali salts and ammonium salts are employed as water-soluble forms of these. Alkali salts are preferred, and sodium salts are more preferred.

<Size of DNA Complex>

The DNA complex 1 preferably has a number-average particle size of 10 μm or more. This can reduce the pressure drop during liquid flow when the DNA complex 1 is used as an adsorbent in an adsorption column, a purification system, or waste fluid or polluted water treatment described later, and prevent the DNA complex 1 from flowing out of the system. Although described in detail later, when the DNA complex 1 is used in these applications, a filter or the like is used to prevent the DNA complex 1 on which the target material to be removed is adsorbed from flowing out of the system. The pore size of the filter depends on the particle size of the DNA complex 1 and is preferably smaller than the particle size of the DNA complex 1. A filter with an excessively small pore size undesirably causes an increased pressure drop while liquid passes through the filter. In the embodiments of the present disclosure, the DNA complex 1 has an average particle size of 10 μm or more, which can increase the pore size of a filter to hold the DNA complex 1 in the system and reduce the pressure drop during liquid flow. From the Ergun equation, which represents the relationship between the pressure drop during liquid flow through a column and the particle size of an adsorbent, the DNA complex 1 preferably has an average particle size of 10 μm or more to reduce the pressure drop to 1 MPa/m or less at a linear flow rate of 1 m/h. Furthermore, the DNA complex 1 with a number-average particle size of 10 μm or more can precipitate rapidly from waste fluid or polluted water, thus making solid-liquid separation in batch adsorption efficient.

The DNA complex 1 preferably has a number-average particle size of 2000 μm or less. This can increase the specific surface area of the DNA complex 1 and enables efficient adsorption of the target material to be removed. For example, the DNA complex 1 to be charged into an adsorption column preferably has a smaller number-average particle size. This is because the surface area of the DNA complex 1 per volume of the adsorption column is increased. For the DNA complex 1 made of a porous body, the target material to be removed can diffuse between particles or through pores of the DNA complex 1 and can be adsorbed on the region other than the outer surface of the DNA complex 1. The DNA complex 1 with an average particle size of 2000 μm or less can have improved adsorption efficiency due to the short diffusion length of the target material to be removed between particles or through pores of the DNA complex 1.

The number-average particle size of the DNA complex 1 can be determined by measuring the equivalent circular diameter of each particle in a low-magnification micrograph and calculating the average particle size from the particle size distribution on a number basis. The micrograph can be obtained with an optical microscope, a scanning electron microscope, or a transmission electron microscope. An image is taken at such a magnification that one visual field includes tens to hundreds of particles, and the equivalent circular diameter of each particle is determined in the visual field. Although the number-average particle size may be determined by measurement in a plurality of visual fields, the number-average particle size may be determined in one visual field including a statistically sufficient number of particles. The number-average particle size may be determined by laser diffraction and scattering, dynamic light scattering (DLS), or ultracentrifugation, which measures a difference in settling velocity depending on the particle size.

[Method for Producing DNA Complex]

A method for producing the DNA complex 1 is described below with reference to FIG. 2. A method for producing the DNA complex 1 according to each embodiment of the present disclosure includes the following steps (1) to (3).

(1) The step of preparing a solution of single-stranded DNA (2) The step of bringing a carrier or primary particles constituting the carrier into contact with the solution of single-stranded DNA (3) The step of removing a solvent from the liquid mixture containing the single-stranded DNA and the carrier or primary particles constituting the carrier Each of the steps is described below.

(1) The Step of Preparing a Solution of Single-Stranded DNA (S201)

In the step S201, a solution of the single-stranded DNA 12 (DNA solution) is prepared. More specifically, the single-stranded DNA 12 is dissolved in ion-exchanged water. The solubility of DNA correlates negatively with the molecular weight of DNA. Thus, the single-stranded DNA 12 with an average molecular weight of 500,000 or less can have an increased concentration in the DNA solution. Thus, the carrier 11 or the primary particles 111 can be brought into contact with a large amount of the single-stranded DNA 12 in a step described later, and consequently the DNA complex 1 can contain an increased amount of the DNA 12.

(2) The Step of Bringing a Carrier or Primary Particles Constituting the Carrier into Contact with the Solution of Single-Stranded DNA (S202)

In the step S202, the carrier 11 or the primary particles 111 constituting the carrier 11 is brought into contact with the solution of the single-stranded DNA 12 prepared in the step S201. The contact can be performed by any method, for example, by preparing a dispersion solution of the carrier 11 or the primary particles 111 and mixing the dispersion solution with the solution of the single-stranded DNA 12 prepared in the step S201. In the preparation of the dispersion solution, the coupling agent may be added to the dispersion solution.

(3) The Step of Removing a Solvent from the Liquid Mixture Containing the Single-Stranded DNA and the Carrier or Primary Particles Constituting the Carrier (S203)

In the step S203, a solvent is removed from the liquid mixture containing the single-stranded DNA 12 prepared in the step S202 and the carrier 11 or the primary particles 111. The solvent may be removed by any method, for example, by spray-drying or vacuum drying. When the primary particles 111 are used, the primary particles 111 aggregate or agglomerate and form an aggregate in this step of removing the solvent.

In the steps S202 and S203, the single-stranded DNA 12 is immobilized on the carrier 11 or the primary particles 111 and forms the DNA complex 1. The DNA complex 1 prepared in the step S203 may be washed with ion-exchanged water. After washing with ion-exchanged water or without washing with ion-exchanged water, the DNA complex 1 may be dispersed and stirred in a solution containing a cross-linking component and may be recovered, washed, and dried.

[Adsorbent]

The DNA complex 1 can be used as an adsorbent that adsorbs a material, such as ions containing at least one element selected from the group consisting of metallic elements and iodine, in a liquid. From the perspective of adsorption capacity, the DNA complex 1 is more suitable for an adsorbent for adsorbing ions containing at least one element selected from the group consisting of cesium, strontium, ruthenium, lead, cadmium, zinc, copper, iron, nickel, silver, rhodium, palladium, iridium, and iodine and is particularly suitable for an adsorbent for adsorbing ions containing ruthenium. These elements may be radioactive elements, and the DNA complex 1 is suitable for an adsorbent for purifying a liquid containing radioactive waste (radioactive waste fluid).

The DNA complex 1 may be used as an adsorbent directly or after the particle size and shape are adjusted by granulation or shaping. Alternatively, the DNA complex 1 immobilized on another substrate, such as a sheet, fiber, woven fabric, or nonwoven fabric, may be used as an adsorbent. For granulation, shaping, or immobilization, a binder, such as an organic binder or an inorganic binder, may be added. For a granular adsorbent, the number-average particle size is preferably 500 μm or more.

In the case where an adsorbent according to an embodiment of the present disclosure is used to remove radioactive metal ions or iodine ions in a radioactive waste fluid, the DNA complex 1 preferably has high heat resistance. This is because the adsorbent may be exposed to a high-temperature environment due to decay heat generated by radioactive decay of a radioactive material adsorbed on the adsorbent, for example. The DNA complex 1 also preferably has high radiation resistance. This is because the adsorbent may be exposed to radioactive rays emitted by radioactive decay. The DNA complex 1 with high heat resistance and/or radiation resistance can prevent the DNA 12 from being released from the carrier 11 and can also have a high adsorption capacity for a target material to be removed in the treatment of a radioactive waste fluid. The DNA complex 1 also preferably has high resistance to solvents, such as acidic solvents and alkalic solvents. Due to high resistance to acids, metal ions in a strong acidic waste fluid can be adsorbed. Waste fluids in the metal recovery process are typically acidic solutions. Metal ions adsorbed on the DNA complex 1 can be separated and recovered from the DNA complex 1 using an acid or a chelating agent. The DNA complex 1 also has resistance to alkalis. Thus, the DNA complex 1 can function in an alkaline environment. For example, the DNA complex 1 can be used to immobilize heavy metals in refuse incineration fly ash. To immobilize heavy metals in refuse incineration fly ash, it is necessary to mix the refuse incineration fly ash with a heavy metal immobilizing agent to prevent redissolution of the heavy metals in the fly ash in an alkaline environment. The DNA complex 1 with high acid resistance and/or alkali resistance can prevent the DNA 12 from being released from the carrier 11 and can also have a high adsorption capacity for a target material to be removed in the treatment of a waste fluid or incineration fly ash.

[Adsorption Column]

FIG. 3 is a schematic view of an example of the structure of an adsorption column 21 filled with an adsorbent 26 containing the DNA complex 1. The adsorption column 21 according to an embodiment of the present disclosure includes a column vessel 24 and an adsorbent 26 filled in the column vessel 24. The adsorbent 26 contains the DNA complex 1. As illustrated in FIG. 3, the adsorption column 21 may further include a top filter 22, a bottom filter 23, and column joints 25. The adsorption column 21 has an opening on the sides of the top filter 22 and the bottom filter 23. A liquid flowing from one opening to the other opening can come into contact with the adsorbent 26. Thus, the adsorbent 26 can adsorb a material, such as ions containing at least one element selected from the group consisting of metallic elements and iodine, contained in the liquid. The adsorption column is also referred to as an adsorption tower.

The top filter 22 has the function of preventing the adsorbent 26 filled in the column vessel 24 from scattering in the fluid passing through the column vessel 24. The bottom filter 23 has the function of preventing the charged adsorbent 26 from flowing out of the adsorption column 21. The adsorption column 21 may have no top filter 22 or no bottom filter 23. In such a case, the adsorption column 21 preferably has a smaller opening than the adsorbent 26.

The adsorption column 21 may have any internal structure. Preferably, a liquid passing through the adsorption column 21 comes into full contact with the adsorbent 26 filled in the adsorption column 21 and flows out of the adsorption column 21. For example, a waste fluid may flow radially from the central portion (central axis) of the adsorption column 21 to the periphery The column vessel 24 may be of any shape, for example, cylindrical. The material of the column vessel 24 may be stainless steel or two-phase stainless steel to prevent leakage of a liquid passing through the adsorption column 21, the adsorbent 26, or a target material to be removed adsorbed on the adsorbent 26.

The column joints 25 have the function of being coupled to pipes through which a liquid passing through the adsorption column 21 is supplied or discharged, for example, pipes of a purification system. When pipes are detached from the adsorption column 21, the column joints 25 can also have the function of preventing the leakage of the contents, such as a liquid remaining in the adsorption column 21 and a target material to be removed adsorbed on the adsorbent 26.

When the adsorption column 21 according to the embodiment of the present disclosure is used to remove radioactive metal ions or iodine ions contained in a radioactive waste fluid, the material of the column vessel 24 is preferably a radiation shielding material, for example, a lead shield. Alternatively, the column vessel 24 may be housed in an outer vessel made of the radiation shielding material. Thus, the column vessel 24 is provided with a lead shield that can reduce the amount of radioactive rays emitted from the adsorption column 21 and reduce the exposure dose of operators around the adsorption column 21. The adsorption column 21 may have a vent for discharging hydrogen, which is produced by decomposition of water caused by radiation, from the column vessel 24. In this application, the top filter 22, the bottom filter 23, the column vessel 24, and the column joints 25 are preferably made of a heat-resistant and radiation-resistant material.

[Purification System]

Figure 4:
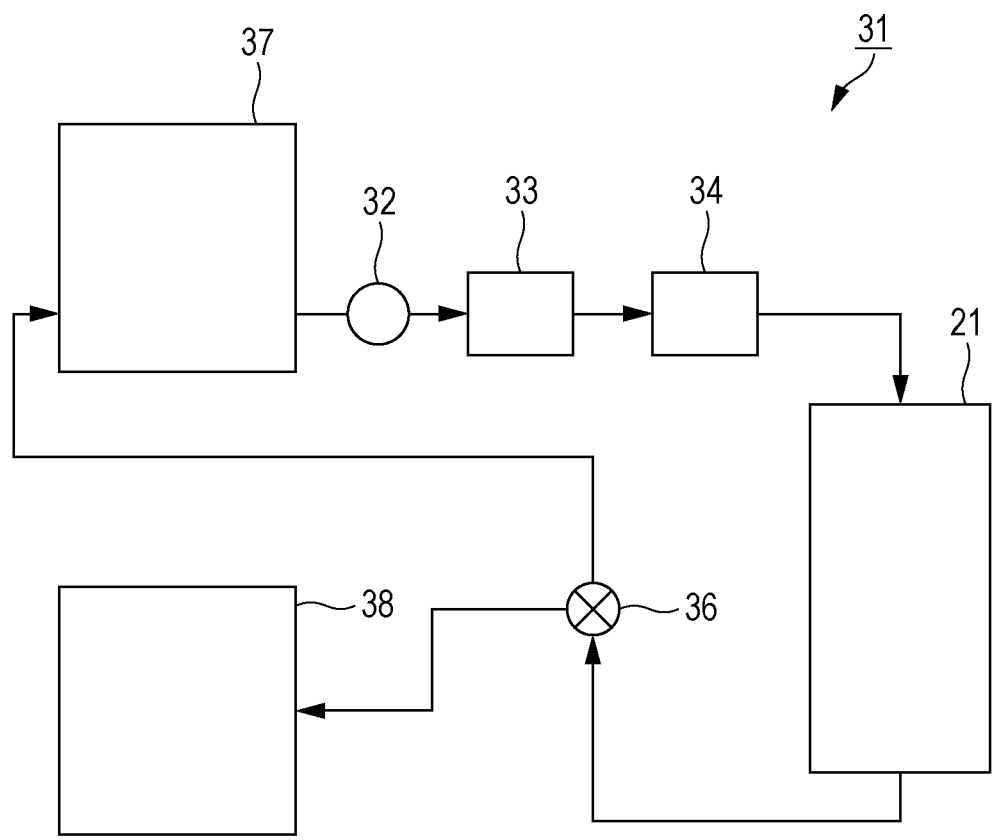
FIG. 4 is a schematic view of an example of the structure of a purification system.

FIG. 4 is a schematic view of an example of the structure of a purification system 31 that includes the adsorption column 21 filled with the adsorbent 26 containing the DNA complex 1. The purification system 31 according to an embodiment of the present disclosure includes the adsorption column 21 and a liquid transfer unit for transferring a liquid to the adsorption column 21. As illustrated in FIG. 4, the purification system 31 may further include a filtration apparatus 33, a pretreatment apparatus 34, a flow path switching valve 36, a waste fluid tank 37, and a treatment liquid tank 38.

A pump 32 is a liquid transfer unit for transferring a liquid to be purified by the purification system 31 to the adsorption column 21. The liquid contains a material, such as ions containing at least one element selected from the group consisting of metallic elements and iodine. The pump 32 can control the amount of liquid to be supplied to the column 21. Although the pump 32 is located upstream of the column 21 in FIG. 4, the pump 32 may be located downstream of the column 21. In the purification system 31 further including the filtration apparatus 33 and the pretreatment apparatus 34, the liquid transfer unit, the pump 32, has the function of transferring liquid to these apparatuses. In this case, the pump 32 may also be placed between the pretreatment apparatus 34 and the adsorption column 21 to stably transfer liquid to the adsorption column 21.

The filtration apparatus 33 removes insoluble solid components from a liquid (typically a waste fluid) supplied to the purification system 31. One example of undesired solid components is particulate matter with a particle size of 1 μm or more.

The pretreatment apparatus 34 performs pretreatment of a liquid supplied to the adsorption column 21. For example, the pretreatment apparatus 34 supplies a pH-adjusting agent to the liquid and mixes the pH-adjusting agent with the liquid. This can control the pH of the liquid to be supplied to the adsorption column 21.

The flow path switching valve 36 switches the flow path of an effluent flowing out of the adsorption column 21. In this embodiment of the present disclosure, the flow path can be switched with the flow path switching valve 36 to resupply an effluent from the adsorption column 21 to the upstream side of the adsorption column 21, thereby passing the liquid through the adsorption column 21 multiple times.

The waste fluid tank 37 stores a liquid to be purified by the purification system 31. The waste fluid tank 37 also has the function of a supply port through which a liquid to be purified by the purification system 31 is supplied to the purification system 31. The treatment liquid tank 38 stores a liquid treated by the purification system 31.

Although the pump 32 is used as a liquid transfer unit in this embodiment of the present disclosure, another liquid transfer unit may be used. The liquid transfer unit may be a liquid transfer unit for transferring liquid by gravity or centrifugal force.

[Liquid Treatment Method]

An example of a liquid treatment method including the use of the DNA complex 1 is described below with reference to FIGS. 4 and 5. A liquid treatment method according to an embodiment of the present disclosure is a method for treating a liquid containing a material, such as ions containing at least one element selected from the group consisting of metallic elements and iodine, and includes the step of bringing the liquid into contact with an adsorbent containing the DNA complex 1. The details are described below.

Figure 5:
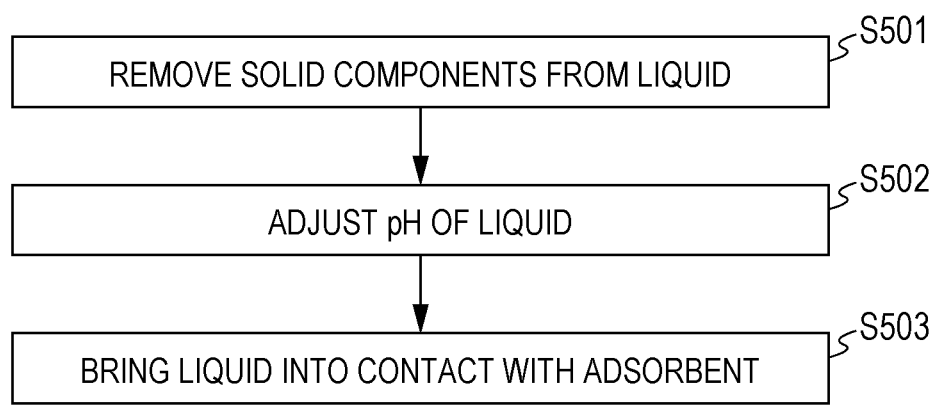
FIG. 5 is a flow chart of an example of a liquid treatment method.

FIG. 5 is a flow chart of the procedures of a liquid treatment method according to an embodiment of the present disclosure. The liquid treatment method according to this embodiment of the present disclosure is a method for bringing a liquid into contact with an adsorbent containing the DNA complex 1 to adsorb and remove a material, such as ions containing at least one element selected from the group consisting of metallic elements and iodine, from the liquid. Thus, the liquid treatment method may also be referred to as a method for purifying a liquid, such as a waste fluid or polluted water containing a target material to be removed.

In the step S501, a liquid (waste fluid or polluted water) to be purified is supplied to the filtration apparatus 33 through a pipe. The filtration apparatus 33 removes insoluble solid components from the liquid.

Next, in the step S502, the liquid from which the solid components are removed is supplied to the pretreatment apparatus 34 through a pipe. In the pretreatment apparatus 34, a pH-adjusting agent is added with stirring to the liquid to adjust the pH of the liquid to the desired pH. The desired pH may be most suitable for the removal of a material to be removed, such as metal ions. For example, Ru may precipitate in an alkaline liquid, and hydrochloric acid is preferably added to a waste fluid to adjust the pH to approximately 2. This is not the case for a low Ru concentration.

Next, in the step S503, the pretreated liquid is supplied to the adsorption column 21 through a pipe. The liquid supplied to the adsorption column 21 passes through the adsorbent 26 in the adsorption column 21. The DNA complex 1 in the adsorbent 26 adsorbs and removes a target material to be removed, such as metal ions, from the liquid to be discharged from the adsorption column 21.

The liquid flowing out of the adsorption column 21 may be transferred to the treatment liquid tank 38 or may be transferred to the waste fluid tank 37 and resupplied to the adsorption column 21.

In the purification system 31 including the pump 32, liquid transfer in the steps S501 to S503 is partly or entirely performed with the pump 32. In the purification system 31 without the filtration apparatus 33 or the pretreatment apparatus 34, the step (the step S501 or S502) performed with these apparatuses is omitted, and the liquid is supplied to the next step.

[Method for Recovering Metal from Liquid]

An example of a method for recovering a metal from a liquid using the DNA complex 1 is described below. The method for recovering a metal from a liquid according to this embodiment of the present disclosure is a method for recovering a metal from a liquid containing a material, such as ions containing at least one element selected from the group consisting of metallic elements and iodine and includes the steps of bringing an adsorbent containing the DNA complex 1 into contact with the liquid and recovering the metal from the adsorbent. The adsorbent may be reused.

Specific examples are described below. A liquid (waste fluid or polluted water) containing ions to be recovered is supplied to an adsorption column through a pipe. The liquid supplied to the adsorption column passes through an adsorbent in the adsorption column. The DNA complex 1 contained in the adsorbent adsorbs a material to be recovered, such as ions, contained in the liquid. The liquid flowing out of the adsorption column may be transferred to a treatment liquid tank or may be transferred to a waste fluid tank and resupplied to the adsorption column.

A method for separating ions to be recovered from an adsorbent containing the DNA complex 1 is described below. For example, the adsorbent containing the DNA complex 1 on which the ions to be recovered are adsorbed can be heated and decomposed to recover the metal. For example, DNA can be heated and decomposed to recover the adsorbed metal ions.

The metal may also be recovered by contact with a liquid (eluent) containing an acid, alkali, or chelating agent. The eluent is supplied to the adsorption column through a pipe. The eluent supplied to the adsorption column passes through the adsorbent in the adsorption column. The material to be recovered, such as ions, is eluted from the DNA complex 1 contained in the adsorbent. The liquid flowing out of the adsorption column may be transferred to a treatment liquid tank or may be transferred to a waste fluid tank and resupplied to the adsorption column. The eluted metal ions may be recovered as hydroxide or chloride.

A washing liquid may be passed through the adsorption column to increase the purity of the ions to be recovered. Impurities weakly adsorbed on the adsorbent can be washed away.

Furthermore, the DNA complex 1 can be reused to recover a metal from a liquid. Thus, metals can be recovered at lower cost than before.

[Method for Treating Heavy Metal in Incineration Fly Ash]

The DNA complex 1 according to the present disclosure can be used as a heavy metal treatment agent for incineration fly ash to immobilize hazardous metals, such as lead, cadmium, zinc, and copper, contained in incineration fly ash discharged during waste incineration. An example of treatment of heavy metals in incineration fly ash using the DNA complex 1 is described below.

In an example of treatment of heavy metals in incineration fly ash according to the present disclosure, the DNA complex 1 according to the present disclosure in a solid powder or slurry form is mixed with incineration fly ash. The amount of the DNA complex 1 ranges from 0.01% to 10% by weight of the incineration fly ash. Preferably, water in an amount of 5% to 50% by weight of the incineration fly ash is mixed with treated incineration fly ash to facilitate disposal of the incineration fly ash.

EXAMPLES

Although the present disclosure is described in detail in the following examples, the present disclosure is not limited to these examples.

(Measurement of Ratio of Single-Stranded DNA)

In the following examples, the ratio of single-stranded DNA to total DNA contained in the resulting DNA complex (sometimes abbreviated to the single-strand ratio) was calculated from the absorbance of an aqueous DNA solution used in preparation of the DNA complex at 260 nm. This relies on the principle that the conversion of double-stranded DNA into single-stranded DNA results in increased absorbance at 260 nm due to the loss of stacking interaction between nucleobases.

More specifically, first, the absorbance (A25) of an aqueous DNA solution is measured at 260 nm at room temperature. Subsequently, the aqueous DNA solution is heated at 95° C. for 30 minutes to unwind double-stranded DNA in the aqueous DNA solution into single-stranded DNA, and the absorbance (A95) is measured again at 260 nm. If the ratio of double-stranded DNA to total DNA in the aqueous DNA solution is 100% by mass, A95/A25 is 1.34. If the ratio of double-stranded DNA to total DNA is 0% by mass, A95/A25 is 1.00. Using this relationship as calibration, the ratio of single-stranded DNA is determined from the absorbance at 25° C. (A25) and the absorbance at 95° C. (A95).

The ratio of single-stranded DNA determined by this method is the ratio of single-stranded DNA in the aqueous DNA solution. In the following examples, this ratio is identical with the ratio of single-stranded DNA to total DNA in a DNA complex. This is because single-stranded DNA in the aqueous DNA solution is unlikely to form double-stranded DNA in the preparation of a DNA complex in the following examples.

This is because firstly the aqueous DNA solution is mixed with a carrier, such as silica, in the preparation of a DNA complex, and multiple portions of single-stranded DNA rather than a single portion thereof are immobilized on the carrier. In DNA immobilized at multiple portions on the carrier, the phosphate group and bases of the DNA backbone are partly covered with the carrier, thus making it difficult to form a base pair with complementary DNA, which is essential to stabilize the double-stranded structure. The balance of the interaction of a stack of bases and repulsive force between phosphate groups is important in stabilizing double-strand formation. In other words, some base pairs must be continuously connected to form double-stranded DNA. Second, a silica solution in the following examples is an alkaline solution with a pH of 9 or more, which is not a preferred neutral environment for the formation of double-stranded DNA.

(Calculation of DNA Content)

In the following examples, the term "DNA content" refers to the mass ratio of DNA to a DNA complex. For example, if 0.1 g of DNA is immobilized in 1 g of a DNA complex, the DNA content is 10% by mass.

In the following examples, the DNA content was determined by absorbance measurement or XPS. In the absorbance method (method using absorbance measurement), the whole washing solution in the preparation of a DNA complex is collected, and the absorbance of the collected solution is measured at 260 nm to determine the amount of DNA in the collected solution. The amount of DNA thus determined is the amount of DNA not immobilized on the carrier in the preparation of the DNA complex and is subtracted from the amount of DNA used in the preparation of the DNA complex to calculate the amount of DNA immobilized on the carrier. In the XPS method (method using XPS), the amount of phosphorus on the surface of the DNA complex is measured and compared with the amount of phosphorus in standard samples to calculate the amount of DNA immobilized on the carrier.

(Measurement of Molecular Weight of DNA)

In the following examples, the molecular weight of DNA refers to the average molecular weight of DNA. The average molecular weight of DNA can be measured by agarose electrophoresis or gel filtration chromatography. In the agarose electrophoresis, the average molecular weight of a sample can be measured by simultaneous electrophoresis of a DNA marker with a known molecular weight. In particular, unlike synthetic DNA with a uniform molecular weight, naturally-occurring DNA of testes of mammals may have a molecular weight distribution. In such a case, a broad DNA band is obtained by electrophoresis. For DNA with a molecular weight distribution, the center of the band is considered to be the average molecular weight. In the gel filtration chromatography, which is a separation technique based on the molecular size, the molecular weight of DNA can be determined using standards with known molecular weights.

(Measurement of Average Particle Size)

In the following examples, the average particle size of the DNA complex was a number-average particle size measured by microscopy. A low-magnification scanning electron micrograph was used to determine the equivalent circular diameter of each particle, from which the number-average particle size was calculated. More specifically, an image was taken at such a magnification that one visual field includes tens to hundreds of particles, and the equivalent circular diameter of each particle was determined in the visual field. For circular particles, the equivalent circular diameter was determined. For non-circular particles, the geometric mean of the maximum diameter and the minimum diameter was determined as the particle size. Assuming that the image represents the whole DNA complex, the number-average particle size was calculated in one visual field.

The average particle size of primary particles constituting an aggregate was the average particle size calculated from the density and the BET specific surface area measured by a gas adsorption method.

(Quantitative Determination of Metal Ions)

In the following examples, metal ions were quantitated by inductively coupled plasma spectroscopy (ICP-AES).

(Designation of DNA Complex)

In the present examples, to easily distinguish DNA complexes, DNA complexes with a silica carrier are also referred to as DNA-immobilized silica. Likewise, DNA complexes with an alumina carrier are also referred to as DNA-immobilized alumina, DNA complexes with a hydrotalcite carrier are also referred to as DNA-immobilized hydrotalcite, and DNA complexes with an activated carbon carrier are also referred to as DNA-immobilized activated carbon.

Example 1

<Immobilization of DNA on Silica>

2.7 g of single-stranded DNA derived from milt of salmon (LS Corporation Co., Ltd., average molecular weight: 50,000) was dissolved in 51.3 g of ion-exchanged water to prepare an aqueous DNA solution (DNA concentration: 5.0% by mass). The ratio of single-stranded DNA in the present example was 89% by mass as measured by the absorbance method.

The pH of 36 g of a colloidal silica (manufactured by Nissan Chemical Industries, Ltd., Snowtex CM, primary particle size: 20 to 25 nm) solution with a solid content of 30% by mass was adjusted to 9.2 with hydrochloric acid. To the solution was added 3.6 g of a solution of a silane compound with a basic functional group represented by the formula (10) (solid content: 15%, this solution is hereinafter referred to as "siloxane solution N1"). After stirring for 30 minutes, the aqueous DNA solution (54 g) was added. The silane compound represented by the formula (10) is in the form of an alkoxy oligomer of a partial hydrolysis condensate thereof and has a degree of polymerization of 10 or more.

The resulting mixed solution of silica and DNA was stirred at room temperature for 60 minutes, and the solvent was removed from the mixed solution with a rotatory evaporator at 70° C. The mixed solution was then dried at 70° C. for 15 hours. The resulting solid was pulverized to prepare approximately 10 g of a DNA-immobilized silica 10.

<Preparation of Reinforcement Treatment Liquid>

5.5 g of a methyl silicate solution (MS56, manufactured by Mitsubishi Chemical Corporation) was added to 24.6 g of methanol. 0.17 g of hydrochloric acid (35%) was added to 24.6 g of ion-exchanged water. These solutions were mixed together and stirred at room temperature for 24 hours to prepare a reinforcement treatment liquid S1.

<Reinforcement Treatment of DNA Complex>

5.5 g of the DNA-immobilized silica 10 was immersed in 54.9 g of the reinforcement treatment liquid Si and was stirred at room temperature for one day. A solid was separated from the reinforcement treatment liquid Si and was washed with 55 g of ion-exchanged water. After washing two times, the solid was dried at 70° C. for two days to prepare approximately 6 g of a DNA-immobilized silica 10S.

<Analysis of DNA Complex>

Figure 7:
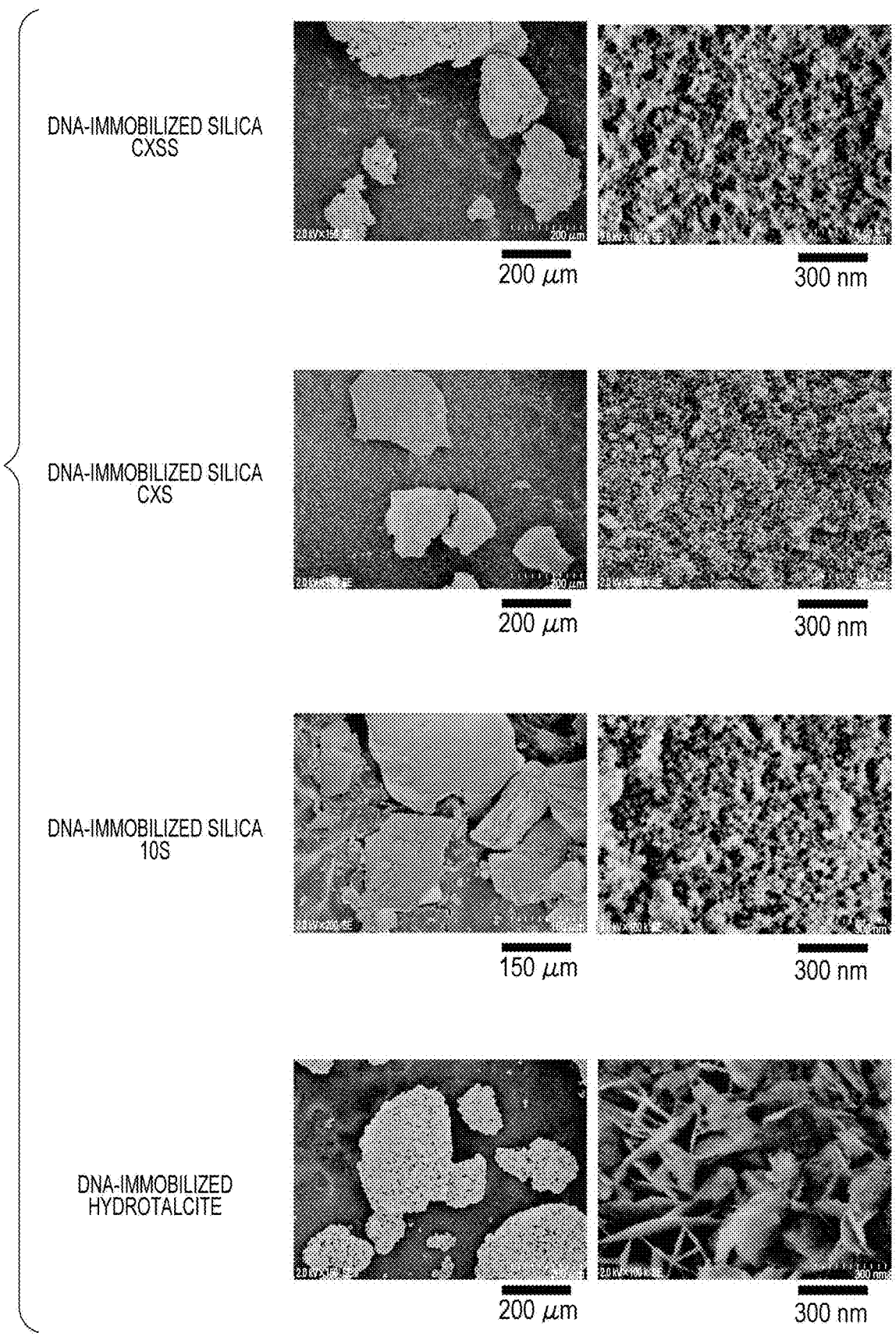
FIG. 7 shows scanning electron micrographs of DNA complexes.

The DNA-immobilized silica 10S had a DNA content of 15.5% by mass as measured by the absorbance method. The DNA-immobilized silica 10S had an average particle size of 156.4 μm when observed with a scanning electron microscope (Hitachi High-Technologies Corporation, S5500) at an accelerating voltage of 2 kV. FIG. 7 shows scanning electron micrographs of the DNA-immobilized silica 10S and other DNA complexes. The DNA-immobilized silica 10S had a porous structure of an aggregate of silica primary particles.

Comparative Example 1

For comparison purposes, a DNA-immobilized silica was prepared in the same manner as in Example 1 except that the single-stranded DNA was replaced with double-stranded DNA (average molecular weight: 6,600,000). The ratio of single-stranded DNA in the present comparative example was 18% by mass as measured by the absorbance method. Although trying to dissolve 2.7 g of double-stranded DNA derived from milt of salmon in 51.3 g of ion-exchanged water in the same manner as in Example 1, the double-stranded DNA was less soluble in water than the single-stranded DNA, and an aqueous DNA solution could not be prepared.

The amount of the double-stranded DNA was decreased to prepare an aqueous DNA solution. It was found that an aqueous DNA solution could be prepared when the concentration of DNA in the aqueous DNA solution was decreased to approximately 1% by mass. Thus, the double-stranded DNA was used to prepare an aqueous DNA solution with a DNA concentration of 1.0% by mass. Although trying to prepare a DNA complex in the same manner as in Example 1, the aqueous DNA solution was difficult to mix with the colloidal silica solution due to its very high viscosity. Consequently, a DNA complex including a sufficient amount of DNA could not be prepared.

Thus, the concentration of DNA was halved to prepare a DNA complex. More specifically, 0.27 g of double-stranded DNA (average molecular weight: 6,600,000) derived from milt of salmon was dissolved in 53.73 g of ion-exchanged water. An aqueous double-stranded DNA solution (the concentration of DNA: 0.5% by weight) thus prepared had a very high viscosity. The aqueous double-stranded DNA solution was used to prepare a DNA complex in the same manner as in Example 1. The resulting DNA-immobilized silica is hereinafter referred to as double-stranded DNA immobilized silica. The double-stranded DNA immobilized silica was subjected to reinforcement treatment in the same manner as in Example 1 to prepare double-stranded DNA immobilized silica S. The DNA content of the double-stranded DNA immobilized silica S was 1.7% by mass as measured by the absorbance method.

Example 2

A DNA-immobilized silica was prepared in the same manner as in Example 1 except that the concentration of DNA in the aqueous DNA solution was 10% by weight. The resulting DNA-immobilized silica is hereinafter referred to as a DNA-immobilized silica 20. The DNA-immobilized silica 20 was subjected to reinforcement treatment in the same manner as in Example 1 to prepare a DNA-immobilized silica 20S. The DNA-immobilized silica 20S had a DNA content of 27.8% by mass as measured by the absorbance method. The concentration of DNA in the aqueous DNA solution could be increased to increase the DNA content of the DNA-immobilized silica.

Example 3

A DNA-immobilized silica was prepared from colloidal silica with a different primary particle size. That is, the DNA-immobilized silica was prepared in the same manner as in Example 1 from colloidal silica with a primary particle size in the range of 10 to 15 nm.

More specifically, a DNA-immobilized silica was prepared in the same manner as in Example 1 except that 48 g of a colloidal silica (Nissan Chemical Industries, Ltd., Snowtex C, primary particle size: 10 to 15 nm) solution with a solid content of 20% by weight was used. The resulting DNA-immobilized silica is hereinafter referred to as a DNA-immobilized silica C1. The DNA-immobilized silica C1 was subjected to reinforcement treatment in the same manner as in Example 1 to prepare a DNA-immobilized silica C1S. The DNA-immobilized silica C1S had a DNA content of 16.1% by mass as measured by the absorbance method.

Example 4

A DNA-immobilized silica was prepared in the same manner as in Example 3 except that the concentration of DNA in the aqueous DNA solution was 10% by weight. The resulting DNA-immobilized silica is hereinafter referred to as a DNA-immobilized silica C2. The DNA-immobilized silica C2 was subjected to reinforcement treatment in the same manner as in Example 3 to prepare a DNA-immobilized silica C2S. The DNA-immobilized silica C2S had a DNA content of 32.3% by mass as measured by the absorbance method. In the same manner as in Example 2, the concentration of DNA in the aqueous DNA solution could be increased to increase the DNA content of the DNA-immobilized silica.

Example 5

A DNA-immobilized silica was prepared from colloidal silica with a different primary particle size. That is, the DNA-immobilized silica was prepared in the same manner as in Example 2 from colloidal silica with a primary particle size in the range of 4 to 6 nm.

More specifically, the colloidal silica solution used in Example 2 was replaced with 72 g of a colloidal silica (Nissan Chemical Industries, Ltd., Snowtex CXS, primary particle size: 4 to 6 nm) solution with a solid content of 15% by weight. A DNA-immobilized silica was prepared in the same manner as in Example 2. The resulting DNA-immobilized silica is hereinafter referred to as a DNA-immobilized silica CXS. The DNA-immobilized silica CXS was subjected to reinforcement treatment in the same manner as in Example 2 to prepare a DNA-immobilized silica CXSS. The DNA-immobilized silica CXSS had a DNA content of 33.1% by mass as measured by the absorbance method. Observation of the DNA-immobilized silica CXSS with a scanning electron microscope in the same manner as in Example 1 showed that the DNA-immobilized silica CXSS had a porous structure of an aggregate of silica primary particles.

[Adsorption Test of Various Materials]

The DNA complexes prepared in Examples 1 to 5 and Comparative Example 1 were subjected to adsorption tests of the following materials.

<Ruthenium Adsorption Test>

The DNA complexes prepared in Examples 1 to 5 and Comparative Example 1 were subjected to a ruthenium adsorption test.

(Preparation of Aqueous Ruthenium Solution)

Ruthenium chloride (Kishida Chemical Co., Ltd., ruthenium (III) chloride n-hydrate) was dissolved in 0.01 N aqueous hydrochloric acid to prepare an aqueous ruthenium solution with a ruthenium concentration of 10 mg/L (10 ppm).

(Batch Adsorption Test)

0.1 g of the DNA complex prepared in each of Examples 1 to 5 and Comparative Example 1 was put into a 15-mL plastic tube, to which 10 mL of the aqueous ruthenium solution was added. After gentle stirring at room temperature, part of the aqueous ruthenium solution was sampled after 24 hours. The sampled aqueous ruthenium solution was centrifuged, and the supernatant was passed through a filter with a pore size of 0.45 µm. The concentration of ruthenium in the aqueous solution was measured by ICP-AES. The rate of removal of ruthenium ions by the DNA complex was calculated from the concentration of ruthenium in the aqueous solution. Table 1 summarizes the results.

<Cesium Adsorption Test>

The DNA complexes prepared in Examples 1 to 5 and Comparative Example 1 were subjected to a cesium adsorption test.

(Preparation of Aqueous Cesium Solution)

Cesium chloride (Kishida Chemical Co., Ltd.) was dissolved in ion-exchanged water, 10% seawater, or 34% seawater to prepare an aqueous cesium solution with a cesium concentration of 20 mg/L (20 ppm). The seawater solution for the preparation of the aqueous cesium solution was an artificial seawater solution prepared by dissolving 36 g of a reagent for the preparation of artificial seawater, Daigo's Artificial Seawater SP (Wako Pure Chemical Industries, Ltd.), in 1 L of ion-exchanged water. This solution was 100% seawater and was diluted 3-fold and 10-fold with ion-exchanged water to prepare 34% and 10% seawater, respectively.

(Batch Adsorption Test)

In the same manner as in the ruthenium adsorption test, 0.1 g of the DNA complex prepared in each of Examples 1 to 5 and Comparative Example 1 was put into a 15-mL plastic tube, to which 10 mL of the aqueous cesium solution was added. After gentle stirring at room temperature, part of the aqueous cesium solution was sampled after 24 hours. The sampled aqueous cesium solution was centrifuged, and the supernatant was passed through a filter with a pore size of 0.45 µm. The concentration of cesium in the aqueous solution was measured by ICP-AES. The rate of removal of cesium ions by the DNA complex was calculated from the concentration of cesium in the aqueous solution. Table 1 summarizes the results.

<Strontium Adsorption Test>

The DNA complexes prepared in Examples 1 to 5 and Comparative Example 1 were subjected to a strontium adsorption test.

(Preparation of Aqueous Strontium Solution)

Strontium chloride hydrate (Kishida Chemical Co., Ltd.) was dissolved in ion-exchanged water, 10% seawater, or 34% seawater to prepare an aqueous strontium solution with a strontium concentration of 2 mg/L (2 ppm). The seawater solution for the preparation of the aqueous strontium solution was the artificial seawater solution prepared for the aqueous cesium solution.

(Batch Adsorption Test)

In the same manner as in the ruthenium adsorption test, 0.1 g of the DNA complex prepared in each of Examples 1 to 5 and Comparative Example 1 was put into a 15-mL plastic tube, to which 10 mL of the aqueous strontium solution was added. After gentle stirring at room temperature, part of the aqueous strontium solution was sampled after 24 hours. The sampled aqueous strontium solution was centrifuged, and the supernatant was passed through a filter with a pore size of 0.45 μm. The concentration of strontium in the aqueous solution was measured by ICP-AES. The rate of removal of strontium ions by the DNA complex was calculated from the concentration of strontium in the aqueous solution. Table 1 summarizes the results.

phate group of the DNA backbone. Thus, the results in Table 1 were obtained because a complex on which free single-stranded DNA is immobilized with nucleobases is more suitable for adsorption and removal of ruthenium.

Although the DNA contents of the DNA complexes (DNA-immobilized silica 20, DNA-immobilized silica C2,

TABLE 1

| | | DNA complex | | | | | | | |
|---|---|---|---|---|---|---|---|---|---|
| | | | | DNA | | | | | |
| | | Carrier Diameter of primary particles | Siloxane solution | Ratio of single-strand DNA | Molecular weight | Concentration (wt %) | Reinforcement treatment | DNA content (wt %) | Particle size (μm) |
| Comparative example 1 | Double-stranded DNA immobilized silica S | 20-25 nm | N1 | 18% | 6,600,000 | 0.5 | S1 | 1.7 | — |
| Example 1 | DNA-immobilized silica 10S | 20-25 nm | N1 | 89% | 50,000 | 5 | S1 | 15.5 | 156.4 |
| Example 2 | DNA-immobilized silica 20 | 20-25 nm | N1 | 89% | 50,000 | 10 | — | — | — |
| Example 2 | DNA-immobilized silica 20S | 20-25 nm | N1 | 89% | 50,000 | 10 | S1 | 27.8 | — |
| Example 3 | DNA-immobilized silica C1S | 10-15 nm | N1 | 89% | 50,000 | 5 | S1 | 16.1 | — |
| Example 4 | DNA-immobilized silica C2 | 10-15 nm | N1 | 89% | 50,000 | 10 | — | — | — |
| Example 4 | DNA-immobilized silica C2S | 10-15 nm | N1 | 89% | 50,000 | 10 | S1 | 32.3 | — |
| Example 5 | DNA-immobilized silica CXS | 4-6 nm | N1 | 89% | 50,000 | 10 | — | — | 169.3 |
| Example 5 | DNA-immobilized silica CXSS | 4-6 nm | N1 | 89% | 50,000 | 10 | S1 | 33.1 | 185 |
| Comparative example 2 | Zeolite A | — | — | — | — | — | — | — | — |

| | | Adsorption test | | | | | | |
|---|---|---|---|---|---|---|---|---|
| | | Ru | Cs | | | Sr | | |
| | | Rate of removal from ion-exchanged water | Rate of removal from ion-exchanged water | Rate of removal from 10% seawater | Rate of removal from 34% seawater | Rate of removal from ion-exchanged water | Rate of removal from 10% seawater | Rate of removal from 34% seawater |
| Comparative example 1 | Double-stranded DNA immobilized silica S | 34.1% | 15.1% | 12.8% | 19.3% | 1.9% | 0.9% | 4.4% |
| Example 1 | DNA-immobilized silica 10S | 83.7% | 74.0% | 14.7% | 23.0% | 96.7% | 14.1% | 15.0% |
| Example 2 | DNA-immobilized silica 20 | 71.3% | — | — | — | — | — | — |
| Example 2 | DNA-immobilized silica 20S | 73.5% | 71.8% | 16.8% | 25.0% | 95.7% | 11.8% | 14.4% |
| Example 3 | DNA-immobilized silica C1S | 74.6% | 73.9% | 14.5% | 19.4% | 99.3% | 30.4% | 19.6% |
| Example 4 | DNA-immobilized silica C2 | 57.7% | — | — | — | — | — | — |
| Example 4 | DNA-immobilized silica C2S | 89.0% | 71.8% | 23.4% | 32.6% | 98.7% | 59.4% | 35.0% |
| Example 5 | DNA-immobilized silica CXS | 68.4% | — | — | — | — | — | — |
| Example 5 | DNA-immobilized silica CXSS | 92.5% | 91.3% | 63.6% | 58.1% | 99.3% | 47.8% | 28.2% |
| Comparative example 2 | Zeolite A | — | 83.7% | 54.0% | 48.8% | — | — | — |

Table 1 shows that the DNA-immobilized silica according to each of Examples 1 to 5 had a higher DNA content and a higher ruthenium removal rate than the double-stranded DNA immobilized silica according to Comparative Example 1. This result shows that the use of single-stranded DNA can provide a DNA complex with a high adsorption capacity for ions containing ruthenium. In particular, ruthenium is probably complexed and adsorbed by nucleobases and the phosphate group of the DNA backbone. Thus, the results in Table 1 were obtained because a complex on which free single-stranded DNA is immobilized with nucleobases is more suitable for adsorption and removal of ruthenium.

Although the DNA contents of the DNA complexes (DNA-immobilized silica 20, DNA-immobilized silica C2, and DNA-immobilized silica CXS) before reinforcement treatment were not measured, these DNA contents are probably higher than the DNA contents of the DNA complexes subjected to reinforcement treatment. This is because the DNA complexes subjected to reinforcement treatment contain components originating from the reinforcement treatment liquid, which relatively decreases the DNA contents.

The DNA-immobilized silica according to each of Examples 1 to 5 had a higher adsorption capacity in the cesium adsorption test and the strontium adsorption test than the double-stranded DNA immobilized silica according to Comparative Example 1.

A comparison between Examples 2, 4, and 5 shows that the adsorption capacity in the ruthenium adsorption test and the cesium adsorption test increases with a decrease in the particle size of primary particles constituting the carrier. In the strontium adsorption test, a high adsorption capacity even in the seawater was achieved when the particle size of primary particles constituting the carrier was 15 nm or less. In particular, the DNA-immobilized silica CXSS (DNA content: 33.1%) had a Ru removal rate of 92.5%, a Cs removal rate in the range of 58.1% to 91.3% (depending on the seawater concentration), and a Sr removal rate in the range of 28.2% to 99.3% (depending on the seawater concentration) and had a much higher adsorption capacity than the double-stranded DNA immobilized silica. These removal rates are equal to or higher than those of zeolite A, which is generally used as a cesium remover (the test results are listed as Comparative Example 2 in Table 1), indicating that these examples reached the practical level as cesium remover materials.

Example 6

In the preparation of DNA-immobilized silica, a washing step was provided before the reinforcement treatment in Example 5.

More specifically, a DNA-immobilized silica CXS was prepared in the same manner as in Example 5, and the resulting solid was washed by the addition of ion-exchanged water and solid-liquid separation. The amount of the ion-exchanged water was 10 times the amount of the solid. The solid was then dried at 70° C. for 15 hours. The solid was pulverized to prepare a DNA-immobilized silica CXSW. The DNA-immobilized silica CXSW was subjected to reinforcement treatment in the same manner as in Example 5 to prepare a DNA-immobilized silica CXSWS. The DNA-immobilized silica CXSWS had a DNA content of 20.0% by mass as measured by the absorbance method.

Example 7

A DNA-immobilized silica was prepared in the same manner as in Example 6 except that no coupling agent (siloxane solution N1) was used.

More specifically, an aqueous DNA solution (27 g) with a DNA concentration of 10% by mass was added to 30 g of a solution of colloidal silica (Nissan Chemical Industries, Ltd., Snowtex CXS, primary particle size: 4 to 6 nm) with a solid content of 15% by weight in Example 6. A DNA-immobilized silica was prepared in the same manner as in Example 6. The resulting DNA-immobilized silica is hereinafter referred to as a DNA-immobilized silica CXSBL. The DNA-immobilized silica CXSBL was subjected to reinforcement treatment in the same manner as in Example 6 to prepare a DNA-immobilized silica CXSBLS. The DNA-immobilized silica CXSBLS had a DNA content of 25.3% by mass as measured by the absorbance method.

Example 8

A DNA-immobilized silica was prepared in the same manner as in Example 6 except that a silane coupling agent with an epoxy group was used as a coupling agent.

More specifically, 0.53 mL of a silane coupling agent with an epoxy group (3-glycidoxypropyltrimethoxysilane, KBM-403, Shin-Etsu Chemical Co., Ltd.) was added to 30 g of a solution of colloidal silica (Nissan Chemical Industries, Ltd., Snowtex CXS, primary particle size: 4 to 6 nm) with a solid content of 15% by weight in Example 6. After stirring for 30 minutes, an aqueous DNA solution (27 g) with a DNA concentration of 10% by mass was added to the solution. A DNA-immobilized silica was prepared in the same manner as in Example 6. The resulting DNA-immobilized silica is hereinafter referred to as a DNA-immobilized silica 403. The DNA-immobilized silica 403 was subjected to reinforcement treatment in the same manner as in Example 6 to prepare a DNA-immobilized silica 403S. The DNA-immobilized silica 403S had a DNA content of 14.8% by mass as measured by the absorbance method.

Examples 9 to 11

A DNA-immobilized silica was prepared in the same manner as in Example 6 except that a silane coupling agent with an amino group was used as a coupling agent.

The silane coupling agent with an amino group was 3-aminopropyltrimethoxysilane (KBM-903, Shin-Etsu Chemical Co., Ltd.) in Example 9 and N-phenyl-3-aminopropyltrimethoxysilane (KBM-573, Shin-Etsu Chemical Co., Ltd.) in Example 10. 3-triethoxysilyl-N-(1,3-dimethylbutylidene)propylamine (KBE-9103, Shin-Etsu Chemical Co., Ltd.) was used in Example 11.

More specifically, 0.53 mL of the silane coupling agent with an amino group was added to 30 g of a solution of colloidal silica (Nissan Chemical Industries, Ltd., Snowtex CXS, primary particle size: 4 to 6 nm) with a solid content of 15% by weight in Example 6. After stirring for 30 minutes, an aqueous DNA solution (27 g) with a DNA concentration of 10% by mass was added to the solution. In Examples 9 and 11, the addition and mixing of the aqueous DNA solution caused gelation of the mixed solution. The gel was washed with water, and the solid was collected and dried at 70° C. to prepare a DNA-immobilized silica 903 and a DNA-immobilized silica 9103. In Example 10, a DNA-immobilized silica 573 was prepared in the same manner as in Example 6. Each DNA-immobilized silica was subjected to reinforcement treatment in the same manner as in Example 6 to prepare a DNA-immobilized silica 903S, a DNA-immobilized silica 9103S, and a DNA-immobilized silica 573S.

[Adsorption Test of Various Materials]

The DNA complexes prepared in Examples 6 to 11 were subjected to adsorption tests of the following materials.

<Ruthenium Adsorption Test>

The DNA complexes prepared in Examples 6 to 11 were subjected to a ruthenium adsorption test.

(Preparation of Aqueous Ruthenium Solution)

An artificial seawater solution was prepared by dissolving 36 g of a reagent for the preparation of artificial seawater, Daigo's Artificial Seawater SP (Wako Pure Chemical Industries, Ltd.), in 1 L of 0.01 N aqueous hydrochloric acid. This solution was 100% seawater and was diluted 3-fold with 0.01 N aqueous hydrochloric acid to prepare 34% seawater.

Ruthenium chloride (Kishida Chemical Co., Ltd., ruthenium (III) chloride n-hydrate) was dissolved in 34% seawater to prepare an aqueous ruthenium solution containing 34% seawater with a ruthenium concentration of 10 mg/L (10 ppm).

(Batch Adsorption Test)

0.1 g of the DNA complex prepared in each of Examples 6 to 11 was put into a 15-mL plastic tube, to which 10 mL of the aqueous ruthenium solution containing 34% seawater was added. After gentle stirring at room temperature, part of the aqueous ruthenium solution was sampled after 24 hours. The sampled aqueous ruthenium solution was centrifuged, and the supernatant was passed through a filter with a pore size of 0.45 μm. The concentration of ruthenium in the aqueous solution was measured by ICP-AES. The rate of removal of ruthenium ions by the DNA complex was calculated from the concentration of ruthenium in the aqueous solution. Table 2 summarizes the results.

TABLE 2

| | | Siloxane solution | Reinforcement treatment | DNA content (wt %) | Adsorption test Ru Rate of removal from 34% seawater |
|---|---|---|---|---|---|
| Example 5 | DNA-immobilized silica CXSS | N1 | S1 | 33.1 | 88.2% |
| Example 6 | DNA-immobilized silica CXSW | N1 | — | — | 83.4% |
| Example 6 | DNA-immobilized silica CXSWS | N1 | S1 | 20.0 | 75.0% |
| Example 7 | DNA-immobilized silica CXSBL | — | — | — | 91.3% |
| Example 7 | DNA-immobilized silica CXSBLS | — | S1 | 25.3 | 81.5% |
| Example 8 | DNA-immobilized silica 403 | 403 | — | — | 87.9% |
| Example 8 | DNA-immobilized silica 403S | 403 | S1 | 14.8 | 76.3% |
| Example 9 | DNA-immobilized silica 903 | 903 | — | — | 77.9% |
| Example 9 | DNA-immobilized silica 903S | 903 | S1 | — | 75.0% |
| Example 10 | DNA-immobilized silica 573 | 573 | — | — | 85.1% |
| Example 10 | DNA-immobilized silica 573S | 573 | S1 | — | 81.2% |
| Example 11 | DNA-immobilized silica 9103 | 9103 | — | — | 81.2% |
| Example 11 | DNA-immobilized silica 9103S | 9103 | S1 | — | 76.3% |

A comparison between Examples 5 and 6 shows that although the washing step before reinforcement treatment decreased the DNA content of the DNA complex, the DNA complex that had a high Ru adsorption capacity even in 34% seawater could be prepared.

Furthermore, the DNA complex that had a high Ru adsorption capacity even in 34% seawater could be prepared even when a siloxane solution serving as a coupling agent was changed as in the above examples or without using the coupling agent.

Example 12

A DNA-immobilized alumina was prepared in the same manner as in Example 1 using alumina as a carrier.

More specifically, the colloidal silica solution was replaced with 30 g of an alumina sol (Nissan Chemical Industries, Ltd., Aluminasol 200, primary particle size: 7 to 15 nm) solution with a solid content of 10% by weight. An aqueous DNA solution (54 g) with a DNA concentration of 5.0% by mass was added to the alumina sol solution. A DNA-immobilized alumina was prepared in the same manner as in Example 1. The DNA-immobilized alumina was subjected to reinforcement treatment in the same manner as in Example 1 to prepare a DNA-immobilized alumina S. The DNA-immobilized alumina S had a DNA content of 21.5% by mass as measured by XPS.

Example 13

A DNA-immobilized hydrotalcite was prepared in the same manner as in Example 2 using hydrotalcite as a carrier.

More specifically, the colloidal silica solution was replaced with 5.89 g of hydrotalcite (Kyowa Chemical Industry Co., Ltd., Kyoward 500 (Kyoward is a trademark of Kyowa Chemical Industry Co., Ltd.)). An aqueous DNA solution (54 g) with a DNA concentration of 10% by mass was added to the hydrotalcite. A DNA-immobilized hydrotalcite was prepared in the same manner as in Example 2. The DNA-immobilized hydrotalcite had a DNA content of 11.4% by mass as measured by the absorbance method.

Example 14

A DNA-immobilized cationic silica was prepared in the same manner as in Example 1 using cationic silica as a carrier.

More specifically, the colloidal silica solution was replaced with 30 g of a surface cationic acidic sol (Nissan Chemical Industries, Ltd., ST-AK) solution with a solid content of 20% by weight. ST-AK is an acidic sol of cationic silica with a primary particle size in the range of 10 to 15 nm. An aqueous DNA solution (54 g) with a DNA concentration of 5.0% by mass was added to the acidic sol solution. A DNA-immobilized cationic silica was prepared in the same manner as in Example 1. The addition of the aqueous DNA solution to the acidic sol immediately formed a precipitate probably due to the formation of a complex of cationic silica and DNA. The DNA-immobilized cationic silica was subjected to reinforcement treatment in the same manner as in Example 1 to prepare a DNA-immobilized cationic silica S. The DNA-immobilized cationic silica S had a DNA content of 36.6% by mass as measured by the absorbance method.

Example 15

A DNA-immobilized activated carbon was prepared using activated carbon as a carrier.

More specifically, 6.0 g of activated carbon (Kuraray Co., Ltd., Kuraray Coal GW-H10/32, coconut shell granular) was added to 40 g of ion-exchanged water to prepare an activated carbon dispersion liquid, to which the aqueous DNA solution (54 g) with a DNA concentration of 10% by mass in Example 2 was added.

The resulting liquid mixture of activated carbon and DNA was stirred at room temperature for 15 hours, and the solid was separated and recovered from the solution and was washed with 60 g of ion-exchanged water. After washing two times, the solid was dried at 80° C. for two days to prepare approximately 6 g of a DNA-immobilized activated carbon. The DNA-immobilized activated carbon had a DNA content of 11.6% by mass as measured by the absorbance method.

Example 16

A DNA-immobilized fumed silica was prepared using fumed silica as a carrier.

More specifically, 3.6 g of the siloxane solution N1 was added to 48 g of a fumed silica dispersion solution (Nippon Aerosil Co., Ltd., AERODISP W 7520 (AERODISP is a trademark of Evonik Industries AG.), primary particle size: 12 nm) with a solid content of 20% by weight and was stirred for 30 minutes. An aqueous DNA solution (54 g) with a DNA concentration of 10% by mass was added to the solution. The resulting liquid mixture of fumed silica and DNA was stirred at room temperature for 60 minutes, and the solvent was removed from the liquid mixture with a rotatory evaporator at 70° C. The resulting solid was washed by the addition of ion-exchanged water and solid-liquid separation. The amount of the ion-exchanged water was 10 times the amount of the solid. The solid was then dried at 70° C. for 15 hours. The solid was pulverized to prepare a DNA-immobilized fumed silica. The DNA-immobilized fumed silica was subjected to reinforcement treatment in the same manner as in Example 1. The resulting DNA-immobilized fumed silica is hereinafter referred to as a DNA-immobilized fumed silica S. The DNA-immobilized fumed silica S had a DNA content of 15.4% by mass as measured by the absorbance method.

[Adsorption Test of Various Materials]

The DNA complexes prepared in Examples 5 and 12 to 16 were subjected to adsorption tests of the following materials.

<Ruthenium Adsorption Test>

The DNA complexes prepared in Examples 5 and 12 to 16 were subjected to a ruthenium adsorption test.

Batch Adsorption Test 0.1 g of the DNA complex prepared in each of Examples 5 and 12 to 16 was put into a 15-mL plastic tube, to which 10 mL of the aqueous ruthenium solution was added. The aqueous ruthenium solution was the 10 ppm aqueous ruthenium solution prepared by dissolving ruthenium chloride in 0.01 N hydrochloric acid or an aqueous ruthenium solution containing 34% seawater. After gentle stirring at room temperature, part of the aqueous ruthenium solution was sampled after 1 or 24 hours. The sampled aqueous ruthenium solution was centrifuged, and the supernatant was passed through a filter with a pore size of 0.45 μm. The concentration of ruthenium in the aqueous solution was measured by ICP-AES. The rate of removal of ruthenium ions by the DNA complex was calculated from the concentration of ruthenium in the aqueous solution. Table 3 summarizes the results.

<Cesium Adsorption Test and Strontium Adsorption Test>

The DNA complexes prepared in Examples 5 and 12 to 16 were subjected to the cesium adsorption test and the strontium adsorption test performed by the method described in Examples 1 to 5. Table 3 summarizes the results.

TABLE 3

| | | DNA complex | | | | Adsorption test Ru | | |
| | | | | | | Rate of removal | Rate of removal | Rate of removal |
| | | Carrier Material | Reinforcement treatment | DNA content (wt %) | Particle size (μm) | from ion-exchanged water | from 34% seawater (1 h) | from 34% seawater (24 h) |
|---|---|---|---|---|---|---|---|---|
| Example 5 | DNA-immobilized silica CXSS | Colloidal silica | S1 | 33.1 | 185 | 92.5% | 49.9% | 88.2% |
| Example 12 | DNA-immobilized alumina | Alumina | — | — | — | 60.5% | — | — |
| Example 12 | DNA-immobilized alumina S | Alumina | S1 | 21.5 | — | 32.2% | — | — |
| Example 13 | DNA-immobilized hydrotalcite | Hydrotalcite | — | 11.4 | 215.3 | 96.2% | 99.0% | >99.9% |
| Example 14 | DNA-immobilized cationic silica | Cationic silica | — | — | — | 57.1% | — | — |
| Example 14 | DNA-immobilized cationic silica S | Cationic silica | S1 | 36.6 | — | 58.3% | — | — |
| Example 15 | DNA-immobilized activated carbon | Activated carbon | — | 11.6 | — | — | — | 89.3% |
| Example 16 | DNA-immobilized fumed silica | Fumed silica | — | — | — | — | — | 81.8% |
| Example 16 | DNA-immobilized fumed silica S | Fumed silica | S1 | 15.4 | — | — | — | 71.0% |

TABLE 3-continued

| | | Adsorption test | | | | | |
| --- | --- | --- | --- | --- | --- | --- | --- |
| | | Cs | | | Sr | | |
| | | Rate of removal from ion-exchanged water | Rate of removal from 10% seawater | Rate of removal from 34% seawater | Rate of removal from ion-exchanged water | Rate of removal from 10% seawater | Rate of removal from 34% seawater |
| Example 5 | DNA-immobilized silica CXSS | 91.3% | 63.6% | 58.1% | 99.3% | 47.8% | 28.2% |
| Example 12 | DNA-immobilized alumina | — | — | — | — | — | — |
| Example 12 | DNA-immobilized alumina S | 6.4% | 20.3% | 30.7% | 10.5% | 14.8% | 15.0% |
| Example 13 | DNA-immobilized hydrotalcite | — | — | — | — | — | — |
| Example 14 | DNA-immobilized cationic silica | 16.6% | 23.5% | 36.1% | 95.1% | 34.6% | 34.6% |
| Example 14 | DNA-immobilized cationic silica S | 36.6% | 18.0% | 26.0% | 93.6% | 20.2% | 22.3% |
| Example 15 | DNA-immobilized activated carbon | — | — | — | — | — | — |
| Example 16 | DNA-immobilized fumed silica | — | — | — | — | — | — |
| Example 16 | DNA-immobilized fumed silica S | — | — | — | — | — | — |

The Ru, Cs, and Sr removal rates were lower in the DNA-immobilized alumina S than in the DNA-immobilized silica CXSS. This is probably because nucleobases and the phosphate group of DNA, which are adsorption sites of various ions, are blocked with the surface of the alumina carrier due to a strong interaction between the alumina surface and DNA.

The DNA-immobilized hydrotalcite, which had a relatively low DNA content of 11.4% by mass, had a very high ruthenium removal rate. This is probably due to the adsorption of ruthenium on the layered compound hydrotalcite in addition to the adsorption of ruthenium on DNA. The DNA-immobilized hydrotalcite had a Ru removal rate of 99.9% or more even in 34% seawater (the residual Ru was below the detection limit of ICP-AES) and had a very high adsorption capacity.

As shown in Examples 14 to 16, DNA complexes with a high adsorption capacity for ions such as Ru could be prepared even when the carrier was change to cationic silica, activated carbon, or fumed silica.

<Iodine Adsorption Test>

The DNA complexes prepared in Examples 5 and 12 to 14 were subjected to an iodide ion adsorption test and an iodate ion adsorption test.

(Preparation of Aqueous Iodide Solution)

Sodium iodide (Kishida Chemical Co., Ltd.) was dissolved in ion-exchanged water to prepare an aqueous iodide solution with an iodide ion concentration of 10 mg/L (10 ppm).

(Preparation of Aqueous Iodate Solution)

Sodium iodate (Kishida Chemical Co., Ltd.) was dissolved in ion-exchanged water to prepare an aqueous iodate solution with an iodate ion concentration of 10 mg/L (10 ppm).

(Batch Adsorption Test)

0.1 g of the DNA complex prepared in each of Examples 5 and 12 to 14 was put into a 15-mL plastic tube, to which 10 mL of the aqueous iodide solution or the aqueous iodate solution was added. After gentle stirring at room temperature, part of the aqueous iodide solution or the aqueous iodate solution was sampled after 24 hours. The sampled aqueous iodide solution or aqueous iodate solution was centrifuged, and the supernatant was passed through a filter with a pore size of 0.45 μm. The concentration of iodide ions or iodate ions in the aqueous solution was measured by ICP-AES. The iodide ion and iodate ion removal rates of each DNA complex were calculated from the concentrations of iodide ions and iodate ions in the aqueous solution. Table 4 summarizes the results.

TABLE 4

| | | | | | | Adsorption test I | |
| --- | --- | --- | --- | --- | --- | --- | --- |
| | | DNA complex | | | | Removal rate of iodide ion | Removal rate of iodate ion |
| | | Carrier Material | Reinforcement treatment | DNA content (wt %) | Particle size (μm) | | |
| Example 5 | DNA-immobilized silica CXSS | Colloidal silica | S1 | 33.1 | 185 | 7.5% | 8.6% |
| Example 12 | DNA-immobilized alumina S | Alumina | S1 | 21.5 | — | 84.1% | 89.3% |

TABLE 4-continued

| | | DNA complex | | | | Adsorption test I | |
|---|---|---|---|---|---|---|---|
| | | Carrier Material | Reinforcement treatment | DNA content (wt %) | Particle size (μm) | Removal rate of iodide ion | Removal rate of iodate ion |
| Example 13 | DNA-immobilized hydrotalcite | Hydrotalcite | — | 11.4 | 215.3 | 57.4% | 81.7% |
| Example 14 | DNA-immobilized cationic silica | Cationic silica | — | — | — | 5.6% | 5.3% |
| Example 14 | DNA-immobilized cationic silica S | Cationic silica | S1 | 36.6 | — | 12.5% | 8.1% |
| Comparative example 2 | Zeolite A | — | — | — | — | 2.4% | 2.7% |

Iodide ions and iodate ions are anions and therefore do not have a very strong interaction with nucleobases and the phosphoric acid of DNA It was found, however, that the DNA complexes had an adsorption capacity for iodide ions and iodate ions. In particular, the DNA-immobilized alumina S and the DNA-immobilized hydrotalcite had iodide ion and iodate ion removal rates much higher than those of zeolite according to Comparative Example 2 and had a practical capacity.

[Performance Comparison with Chelate Resin and Anion-Exchange Resin]

The DNA-immobilized silica CXSS prepared in Example 5 and the DNA-immobilized hydrotalcite prepared in Example 13 were compared in performance tests with a commercial chelate resin and a commercial anion-exchange resin widely used to remove heavy metals.

<Ruthenium Adsorption Test>

The DNA-immobilized silica CXSS, the DNA-immobilized hydrotalcite, a chelate resin (Diaion CRB05, Mitsubishi Chemical Corporation), and an anion-exchange resin (Diaion WA30, Mitsubishi Chemical Corporation) were subjected to the ruthenium adsorption test.

(Preparation of Aqueous Ruthenium Solution Containing Seawater)

An artificial seawater solution was prepared by dissolving 36 g of a reagent for the preparation of artificial seawater, Daigo's Artificial Seawater SP (Wako Pure Chemical Industries, Ltd.), in 1 L of 0.01 N aqueous hydrochloric acid. This solution was 100% seawater and was diluted 3-fold with 0.01 N aqueous hydrochloric acid to prepare 34% seawater.

Ruthenium chloride (Kishida Chemical Co., Ltd., ruthenium (III) chloride n-hydrate) was dissolved in 34% seawater to prepare an aqueous ruthenium solution containing 34% seawater with a ruthenium concentration of 10 mg/L (10 ppm).

(Batch Adsorption Test)

0.1 g of each sample was put into a 15-mL plastic tube, to which 10 mL of the aqueous ruthenium solution containing 34% seawater was added. After gentle stirring at room temperature, part of the aqueous ruthenium solution was sampled after 1 or 24 hours. The sampled aqueous ruthenium solution was centrifuged, and the supernatant was passed through a filter with a pore size of 0.45 μm. The concentration of ruthenium in the aqueous solution was measured by ICP-AES. The rate of removal of ruthenium ions by each sample was calculated from the concentration of ruthenium in the aqueous solution. Table 5 summarizes the results.

(Column Flow Test)

A ruthenium removal test was performed by filling a column with each sample and supplying the column with the aqueous ruthenium solution (34% seawater).

A glass column with an inner diameter of 10 mm was filled with 1 mL of each sample. The aqueous ruthenium solution containing 34% seawater was passed through the column with a tube pump at a flow rate of 2 mL/min (space velocity: 120/h). Influent water flowing into the column and effluent water flowing out of the column were sampled at regular intervals. The concentration of ruthenium in these samples was measured to prepare a breakthrough curve of ruthenium.

Figure 6A:
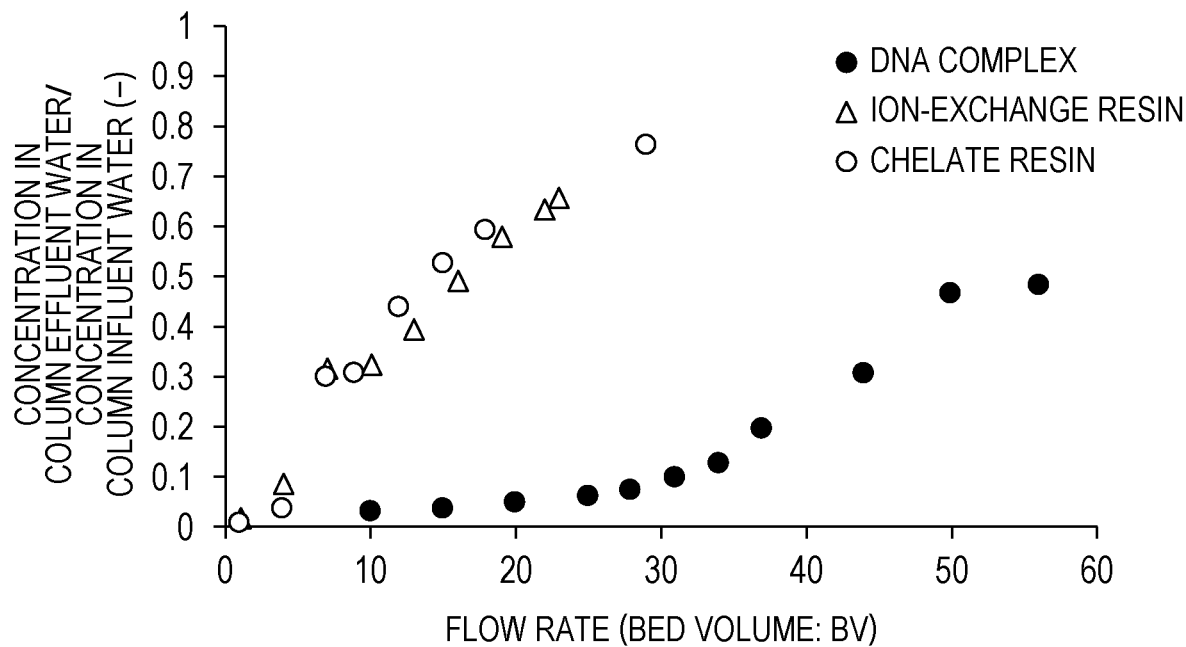
FIG. 6A is a graph of the results of a column flow test on a DNA complex.
Figure 6B:
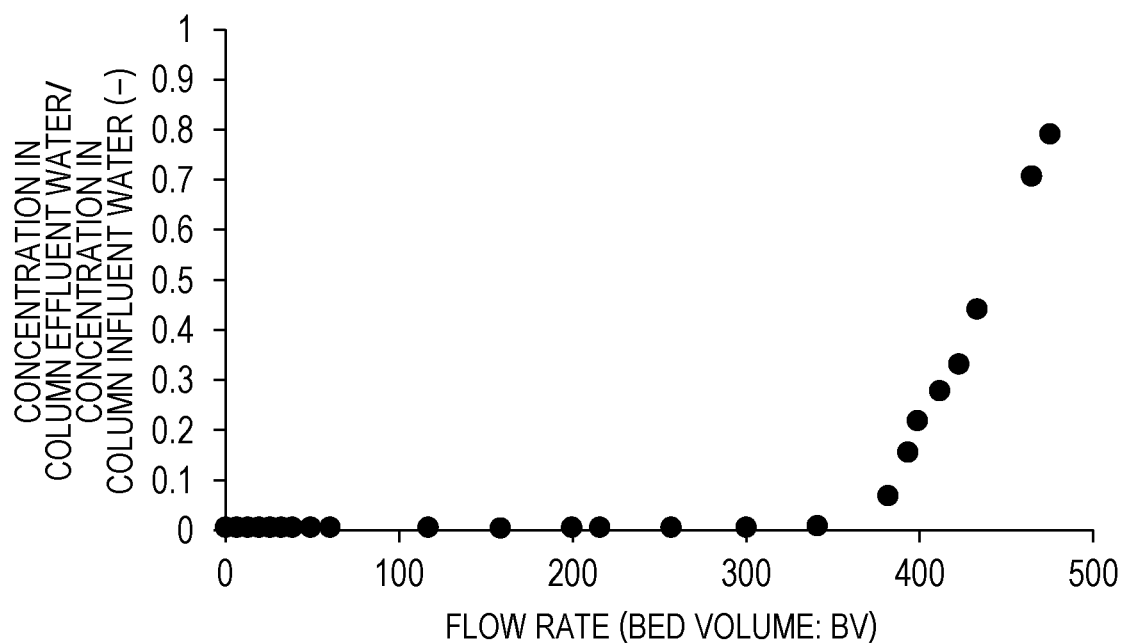
FIG. 6B is a graph of the results of a column flow test on a DNA complex.

FIGS. 6A and 6B are the breakthrough curves of ruthenium. In FIGS. 6A and 6B, the vertical axis represents the value of the concentration of ruthenium in the column effluent water divided by the concentration of ruthenium in the column influent water (concentration in column effluent water/concentration in column influent water). The value is zero when ruthenium is completely removed from the column and is one when ruthenium remains wholly in the column. The horizontal axis represents the flow rate expressed in bed volume (BV), which is the ratio of the volume of the ruthenium solution flowing through to the volume of the DNA complex. FIG. 6A shows the results of the DNA-immobilized silica CXSS, and FIG. 6B shows the results of the DNA-immobilized hydrotalcite.

In the present example, the bed volume was determined at a breakthrough point (10% breakthrough point) at which the concentration in column effluent water is 10% of the concentration in column influent water (BV at 10% breakthrough point). A larger bed volume is indicative of a larger amount of ruthenium solution that can be subjected to removal treatment and a higher removal capacity. Table 5 summarizes the BVs at the 10% breakthrough point.

TABLE 5

| | | DNA complex | | | Batch adsorption test Ru | | Column flow test Ru |
| | | Carrier Material | DNA content (wt %) | Particle size (μm) | Rate of removal from 34% seawater (1 h) | Rate of removal from 34% seawater (24 h) | BV at 10% breakthrough point |
|---|---|---|---|---|---|---|---|
| Example 5 | DNA-immobilized silica CXSS | Colloidal silica | 33.1 | 185 | 49.9% | 88.2% | 31.8 |
| Example 13 | DNA-immobilized hydrotalcite | Hydrotalcite | 11.4 | 215.3 | 99.0% | >99.9% | 387.6 |
| Comparative example 3 | Chelate resin | — | — | — | 13.7% | 37.5% | 5.4 |
| Comparative example 4 | Anion-exchange resin | — | — | — | 15.7% | 72.2% | 4.3 |

Table 5 shows that the DNA-immobilized silica CXSS and the DNA-immobilized hydrotalcite have a higher adsorption capacity than the chelate resin and the anion-exchange resin widely used to remove heavy metals.

As is clear from FIGS. 6A and 6B and Table 5, the BVs at the 10% breakthrough point were 31.8 for the DNA-immobilized silica CXSS and 387.6 for the DNA-immobilized hydrotalcite. Under the conditions of the present examples, this indicates that the amount of aqueous ruthenium solution that can be treated is approximately 32 or 388 times the volume of the DNA complex charged. Under the conditions of the present examples, the commercial chelate resin and ion-exchange resin according to the comparative examples had a BV in the range of approximately 4.3 to 5.4 at the 10% breakthrough point. Comparing with these BVs, the DNA complexes according to the present examples have a practical ruthenium removal capacity.

It is known that a relatively minute amount of ions is difficult to remove from seawater, which contains large amounts of sodium, calcium, and other ions. As shown in Table 3, the DNA complexes according to the present examples retained their ruthenium removal capacities for seawater as compared with for the seawater-free system.

These results show that the DNA complexes according to the present example can selectively remove ruthenium and have a practical removal capacity.

Example 17

For the DNA-immobilized silica CXSBL prepared in Example 7, an adsorption isotherm was prepared to determine the saturated adsorption amount of ruthenium. More specifically, 0.1 g of the DNA-immobilized silica CXSBL was put into a 15-mL plastic tube, to which 10 mL of the aqueous ruthenium solution containing 34% seawater was added. The concentration of ruthenium in the solution ranged from 5 to 2000 ppm. After gentle stirring at room temperature, part of the aqueous ruthenium solution was sampled after 24 hours. The sampled aqueous ruthenium solution was centrifuged, and the supernatant was passed through a filter with a pore size of 0.45 μm. The concentration of ruthenium in the solution was measured by ICP-AES. The equilibrium concentration of ruthenium and the amount of adsorbed ruthenium were calculated from the concentration of ruthenium in the aqueous solution. Table 6 shows the results. As is clear from Table 6, the adsorption was Langmuir adsorption, and the saturated adsorption amount was 59 mg/g as determined from the Langmuir adsorption isotherm.

TABLE 6

| Equilibrium ruthenium concentration (mg/L) | Amount of adsorbed ruthenium (mg/g) |
|---|---|
| 0.58 | 0.35 |
| 0.65 | 0.88 |
| 1.43 | 5.24 |
| 3.57 | 10.69 |
| 22.44 | 24.24 |
| 104.72 | 42.74 |
| 486.20 | 57.80 |
| 1482.40 | 56.78 |

Example 18

The ruthenium removal rate of the DNA-immobilized hydrotalcite prepared in Example 13 was determined at different concentrations of ruthenium in the solution. More specifically, 0.1 g of the DNA-immobilized hydrotalcite was put into a 15-mL plastic tube, to which 10 mL of the aqueous ruthenium solution containing 34% seawater was added. The concentration of ruthenium ranged from 5 to 2000 ppm. After gentle stirring at room temperature, part of the aqueous ruthenium solution was sampled after 24 hours. The sampled aqueous ruthenium solution was centrifuged, and the supernatant was passed through a filter with a pore size of 0.45 μm. The concentration of ruthenium in the solution was measured by ICP-AES. The concentration of ruthenium in the solution without the adsorbent and the concentration of ruthenium in the solution containing the DNA-immobilized hydrotalcite were measured, and the ruthenium removal rate was calculated. Table 7 shows the results. As is clear from Table 7, the DNA-immobilized hydrotalcite can efficiently remove ruthenium from the seawater solution at low to high concentrations.

TABLE 7

| Concentration of ruthenium in seawater solution without adsorbent (ppm) | Concentration of ruthenium in seawater solution to which DNA-immobilized hydrotalcite is added (ppm) | Ruthenium removal rate (%) |
|---|---|---|
| 4.05 | 0.00 | 100.00 |
| 9.42 | 0.03 | 99.64 |
| 53.79 | 0.31 | 99.43 |
| 110.43 | 0.68 | 99.38 |
| 264.86 | 0.24 | 99.91 |
| 1064.20 | 0.10 | 99.99 |
| 2050.20 | 0.20 | 99.99 |

Example 19

A batch adsorption test of various metal ions was performed with the DNA-immobilized silica CXSBL prepared in Example 7.

An aqueous palladium solution was prepared by dissolving palladium chloride in a 0.01 N aqueous hydrochloric acid. An aqueous rhodium solution was prepared by dissolving rhodium chloride in ultrapure water. An aqueous silver solution was prepared by diluting a silver nitrate solution with ultrapure water. An aqueous lead solution was prepared by dissolving lead nitrate in ultrapure water. An aqueous cadmium solution was prepared by dissolving cadmium chloride in ultrapure water. An aqueous zinc solution was prepared by dissolving zinc sulfate in ultrapure water. An aqueous copper solution was prepared by dissolving copper chloride in ultrapure water. An aqueous iron solution was prepared by dissolving iron chloride in ultrapure water. An aqueous nickel solution was prepared by dissolving nickel chloride in ultrapure water. The concentration of metal ions in the solution was 10 ppm.

0.1 g of the DNA-immobilized silica CXSBL prepared in Example 7 was put into a 15-mL plastic tube, to which 10 mL of the aqueous metal ion solution was added. After gentle stirring at room temperature, part of the aqueous metal ion solution was sampled after 24 hours. The sampled aqueous metal ion solution was centrifuged, and the supernatant was passed through a filter with a pore size of 0.45 µm. The concentration of metal ions in the aqueous solution was measured by ICP-AES. The rate of removal of metal ions by the DNA complex was calculated from the concentration of metal ions in the aqueous solution. Table 8 summarizes the results. The DNA complex can efficiently remove heavy metal ions and noble metal ions. The metal ion removal rate in 34% seawater measured in an aqueous metal ion solution containing 34% seawater was 94.5% for palladium, 48.8% for nickel, and 84.9% for zinc. This proved the high adsorption selectivity of the DNA complex for elements of the platinum group, such as ruthenium and palladium.

TABLE 8

| | Rate of removal from aqueous solution (%) |
|---|---|
| Palladium | 95 |
| Rhodium | 85 |
| Silver | 89 |
| Lead | 99 |
| Cadmium | 98 |
| Zinc | 97 |
| Copper | 85 |
| Iron | 42 |
| Nickel | 95 |

Example 20

The DNA-immobilized activated carbon prepared in Example 15 was subjected to an iodide ion adsorption test and an iodate ion adsorption test by the method described above.

0.1 g of the DNA-immobilized activated carbon prepared in Example 15 was put into a 15-mL plastic tube, to which 10 mL of the aqueous iodide solution or the aqueous iodate solution was added. An aqueous solution containing 34% seawater was also used in the same manner. After gentle stirring at room temperature, part of the aqueous iodide solution or the aqueous iodate solution was sampled after 24 hours. The sampled aqueous iodide solution or aqueous iodate solution was centrifuged, and the supernatant was passed through a filter with a pore size of 0.45 µm. The concentration of iodide ions or iodate ions in the aqueous solution was measured by ICP-AES. The iodide ion and iodate ion removal rates of each DNA-immobilized activated carbon were calculated from the concentrations of iodide ions and iodate ions in the aqueous solution. Table 9 summarizes the results.

TABLE 9

| | Rate of removal from aqueous solution (%) | Rate of removal from 34% seawater (%) |
|---|---|---|
| Iodide | 92.6 | 26.1 |
| Iodate | 56.0 | 38.8 |

Example 21

The DNA-immobilized silica CXSWS prepared in Example 6 was compared in a performance test with a commercial ion-exchange resin widely used to recover metals.

<Ruthenium and Iridium Adsorption Test in Strong Acidic Solution>

The DNA-immobilized silica CXSWS prepared in Example 6 was subjected to a ruthenium or iridium adsorption test in a strong acidic solution. For comparison purposes, an anion-exchange resin (Diaion SA20A, Mitsubishi Chemical Corporation) was used.

(Batch Adsorption Test in Strong Acidic Solution)

0.05 g of the DNA-immobilized silica CXSWS prepared in Example 6 or the anion-exchange resin was put into a 15-mL plastic tube, to which 5 mL of a ruthenium hydrochloric acid solution or an iridium hydrochloric acid solution was added. The ruthenium hydrochloric acid solution has a hydrochloric acid concentration of 3% and contains 2 ppm of ruthenium ions, 2 ppm of platinum ions, 2 ppm of iron ions, and 10000 ppm of sodium chloride. The iridium hydrochloric acid solution contains iridium ions instead of ruthenium ions in the ruthenium hydrochloric acid solution. Ruthenium (III) chloride hydrate was used for ruthenium, and hexachloroiridium (IV) acid hydrate was used for iridium.

After gentle stirring in the plastic tube at room temperature, part of the ruthenium hydrochloric acid solution or iridium hydrochloric acid solution was sampled after 24 hours. The sampled hydrochloric acid solution was centrifuged, and the supernatant was passed through a filter with a pore size of 0.45 µm. The concentration of ruthenium or iridium in the hydrochloric acid solution was measured by ICP-AES. The ruthenium ion or iridium ion adsorption rate of the DNA-immobilized silica CXSWS was calculated from the concentration of ruthenium or iridium in the aqueous solution. Likewise, the platinum ion and iron ion adsorption rates were determined. Table 10 summarizes the results.

The DNA-immobilized silica CXSWS could adsorb ruthenium and iridium in 3% hydrochloric acid. The DNA-immobilized silica CXSWS had almost the same adsorption capacity as the ion-exchange resin. The DNA-immobilized silica CXSWS did not adsorb platinum ions but for iron ions had a higher adsorption rate than the ion-exchange resin. The ion-exchange resin efficiently adsorbed platinum ions. The DNA-immobilized silica CXSWS can efficiently separate ruthenium or iridium from platinum. The DNA-immobilized silica CXSWS had highly selective adsorptivity for ruthenium and iridium relative to platinum.

TABLE 10

| | Hydrochloric acid concentration 3% | |
|---|---|---|
| | Ion-exchange resin SA20A | DNA-immobilized silica CXSWS |
| Ruthenium ion adsorption rate % | 9.4 | 3.1 |
| Platinum ion adsorption rate % | 97.5 | 0 |
| Iron ion adsorption rate % | 1.5 | 35.1 |
| Iridium ion adsorption rate % | 34.2 | 25.7 |
| Platinum ion adsorption rate % | 98.8 | 1.2 |
| Iron ion adsorption rate % | 0.7 | 18.8 |

Example 22

<Recovery Test for Adsorbed Ruthenium and Iridium>

A ruthenium or iridium recovery test was performed with the DNA-immobilized silica CXSWS on which ruthenium or iridium was adsorbed prepared in Example 21.

(Recovery Test)

1 mL of 6 N hydrochloric acid was added to the DNA-immobilized silica CXSWS (0.05 g) on which ruthenium or iridium was adsorbed prepared in Example 21. After gentle stirring at room temperature for 2 hours, the hydrochloric acid solution was sampled. The concentration of ruthenium or iridium in the sampled hydrochloric acid solution was measured by ICP-AES. Adsorbed ruthenium or iridium could be completely recovered. Metal ions adsorbed on the DNA-immobilized silica CXSWS could be recovered using concentrated hydrochloric acid.

Example 23

<Ruthenium Readsorption Test>

A ruthenium readsorption test was performed with the DNA-immobilized silica CXSWS from which ruthenium was recovered (desorbed) in Example 22. An adsorption test performed in the same manner as in Example 21 showed that ruthenium could be readsorbed. The DNA complex could adsorb metal ions, which could be recovered, and could readsorb metal ions. The DNA complex can be used as a reusable adsorbent for metal recovery.

Example 24

<Ruthenium and Palladium Recovery Test>

The DNA-immobilized silica CXSBL prepared in Example 7 was subjected to a ruthenium and palladium recovery test.

(Recovery Test)

0.1 g of the DNA-immobilized silica CXSBL prepared in Example 7 was put into a 15-mL plastic tube, to which 10 mL of an aqueous ruthenium solution (ruthenium concentration: 10 ppm) or an aqueous palladium solution (palladium concentration: 10 ppm) was added (these aqueous solutions contained 34% seawater). After gentle stirring at room temperature, part of the aqueous ruthenium solution or the aqueous palladium solution was sampled after 24 hours. The sampled aqueous ruthenium or palladium solution was centrifuged, and the supernatant was passed through a filter with a pore size of 0.45 µm. The concentration of ruthenium ions or palladium ions in the aqueous solution was measured by ICP-AES. The ruthenium ion and palladium ion adsorption rates of the DNA-immobilized silica CXSBL calculated from the concentrations of ruthenium ions and palladium ions in the aqueous solution were 94.3% and 96.1%, respectively. 10 mL of 1 M sodium ethylenediaminetetraacetate (EDTA) solution, 1 N aqueous hydrochloric acid, or ultrapure water was added to the DNA-immobilized silica CXSBL on which these metal ions were adsorbed, and was left standing at room temperature for three days. Part of these eluates were sampled and centrifuged, and the supernatant was passed through a filter with a pore size of 0.45 µm. The concentrations of ruthenium ions and palladium ions in the eluates were measured by ICP-AES. The ruthenium ion and palladium ion recovery rates calculated from the concentrations of ruthenium ions and palladium ions in the eluates were 23% and 64%, respectively, for the 1 M sodium ethylenediaminetetraacetate (EDTA) solution. The ruthenium ion and palladium ion recovery rates were 20% and 84%, respectively, for the 1 N hydrochloric acid. The ruthenium ion and palladium ion recovery rates were 0.6% and 4%, respectively, for the ultrapure water. These results show that the DNA-immobilized silica CXSBL can adsorb metal ions and that the adsorbed metal ions can be recovered. The eluent for recovery may be an EDTA solution or aqueous hydrochloric acid. The DNA-immobilized silica CXSBL can be used as an adsorbent for metal recovery.

Example 25

The availability of the DNA complexes according to the present examples in incineration fly ash treatment was examined by subjecting the DNA-immobilized silica CXSWS prepared in Example 6 and the DNA-immobilized hydrotalcite prepared in Example 13 to a test on possible immobilization of heavy metal ions contained in incineration fly ash. Lead ions, which are present in high amounts in fly ash, were used as a heavy metal model.

(Batch Adsorption Test in Alkaline Solution)

0.1 g of the DNA-immobilized silica CXSWS prepared in Example 6 or the DNA-immobilized hydrotalcite prepared in Example 13 was put into a 15-mL plastic tube, to which 10 mL of an aqueous lead solution was added. The aqueous lead solution contained 10 ppm of lead and 5000 ppm of coexisting calcium ions and had a pH of 12.

After gentle stirring in the plastic tube at room temperature, part of the aqueous lead solution was sampled after 6 and 24 hours. The sampled solution was centrifuged, and the supernatant was passed through a filter with a pore size of 0.45 μm. The concentration of lead in the solution was measured by ICP-AES. The lead ion adsorption rates of the DNA-immobilized silica CXSWS and the DNA-immobilized hydrotalcite were calculated from the concentration of lead in the aqueous solution. Table 11 shows the results. The DNA-immobilized silica CXSWS and the DNA-immobilized hydrotalcite could adsorb lead ions in a strong alkaline environment and in the presence of calcium ions.

(Redissolution Test of Lead Ions)

A test according to Notification No. 13 of the Environment Agency was simulated to examine the dissolution of heavy metal ions from incineration fly ash. More specifically, 0.1 g of the DNA-immobilized silica CXSWS or the DNA-immobilized hydrotalcite on which lead ions were adsorbed prepared in the batch adsorption test was stirred in 10 mL of water (adjusted to pH 12) for 6 hours. After centrifugation (2150 G, 20 minutes), the resulting supernatant was passed through a 1.2-μm filter, and the concentration of lead in the solution was measured by ICP-AES. The redissolution concentration standard is 0.3 ppm, which should be the upper limit. If adsorbed lead ions are completely dissolved, the redissolution concentration ranges from 6 to 8 ppm.

Table 12 shows the results. The redissolution concentration of lead ions from the DNA-immobilized silica CXSWS or the DNA-immobilized hydrotalcite was 0.3 ppm or less. The results show that lead ions adsorbed on the DNA-immobilized silica CXSWS and the DNA-immobilized hydrotalcite remained mostly undissolved, indicating that the DNA-immobilized silica CXSWS and the DNA-immobilized hydrotalcite are practical agents for treating heavy metals in incineration fly ash.

TABLE 11

| | Lead adsorption rate (%) | |
|---|---|---|
| | Adsorption for 6 hours | Adsorption for 24 hours |
| DNA-immobilized silica CXSWS | 78.1 | 81.4 |
| DNA-immobilized hydrotalcite | 72.3 | 71.3 |

TABLE 12

| | Redissolution concentration of lead in simulated No. 13 test (ppm) |
|---|---|
| DNA-immobilized silica CXSWS | 0.06 |
| DNA-immobilized hydrotalcite | 0.03 |

The present disclosure can provide a DNA complex that can efficiently adsorb a target material from a liquid containing large amounts of impurities.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A DNA complex comprising: a carrier; and DNA immobilized on the carrier,
    wherein 80% or more by mass of the DNA is single-stranded DNA,
    the DNA has an average molecular weight of 500,000 or less,
    the carrier contains an inorganic material,
    the DNA complex has an average particle size of 10 μm or more, the DNA content is more than 15% by mass and 50% or less by mass of the DNA complex, and
    the carrier is an aggregate of primary particles, and
    the primary particles have an average particle size in the range of 1 to 15 nm.

2. A DNA complex comprising: a carrier; and DNA immobilized on the carrier,
    wherein 80% or more by mass of the DNA is single-stranded DNA,
    the DNA has an average molecular weight of 500,000 or less, and
    the carrier contains layered metal hydroxides.

3. The DNA complex according to claim 1, wherein the carrier contains silica.

4. The DNA complex according to claim 1, wherein primary particles are cross-linked through a bond including a siloxane bond.

5. The DNA complex according to claim 2, wherein the DNA complex has an average particle size of 10 μm or more.

6. The DNA complex according to claim 1, wherein the DNA complex has an average particle size of 2000 μm or less.

7. The DNA complex according to claim 2, wherein the DNA content ranges from 1% to 50% by mass of the DNA complex.

8. The DNA complex according to claim 2, wherein the DNA content is more than 15% by mass and 50% or less by mass of the DNA complex.

9. An adsorption column comprising: a column; and an adsorbent filled in the column,
    wherein the adsorbent contains the DNA complex according to claim 1.

10. A purification system comprising: an adsorption column; and a liquid transfer unit for transferring a liquid containing ions containing at least one element selected from the group consisting of metallic elements and iodine into the adsorption column,
    wherein the adsorption column is the adsorption column according to claim 9.

11. A method for treating a liquid containing ions containing at least one element selected from the group consisting of metallic elements and iodine, comprising:
    bringing the liquid into contact with an adsorbent,
    wherein the adsorbent contains the DNA complex according to claim 1.

12. A method for recovering a metal from a liquid containing a metallic element, comprising:
    bringing the liquid into contact with an adsorbent; and
    recovering the metal from the adsorbent,
    wherein the adsorbent contains the DNA complex according to claim 1.

13. A method for treating a heavy metal in incineration fly ash, comprising:
    adding an adsorbent to the incineration fly ash,
    wherein the adsorbent contains the DNA complex according to claim 1.

14. The method for treating a heavy metal in incineration fly ash according to claim 13, further comprising:
adding water to the incineration fly ash.

15. The DNA complex according to claim 2, wherein the DNA complex has an average particle size of 2000 μm or less.

16. The DNA complex according to claim 1, wherein the DNA complex has an average particle size of 500 μm or less.

17. The DNA complex according to claim 2, wherein the DNA complex has an average particle size of 500 μm or less.

* * * * *